(12) United States Patent
Sanchez-Schmitz et al.

(10) Patent No.: US 8,030,070 B2
(45) Date of Patent: *Oct. 4, 2011

(54) ARTIFICIAL LYMPHOID TISSUE EQUIVALENT

(75) Inventors: Guzman Sanchez-Schmitz, Orlando, FL (US); Russell Higbee, Orlando, FL (US); Heather Fahlenkamp, Broken Arrow, OK (US); Darrell J. Irvine, Arlington, MA (US); William L. Warren, Orlando, FL (US); Donald Drake, III, Orlando, FL (US)

(73) Assignee: Sanofi Pasteur Vaxdesign Corp., Orlando, FL (US)

( * ) Notice: Subject to any disclaimer, the term of this patent is extended or adjusted under 35 U.S.C. 154(b) by 306 days.

This patent is subject to a terminal disclaimer.

(21) Appl. No.: 11/471,514

(22) Filed: Jun. 21, 2006

(65) Prior Publication Data

US 2007/0015136 A1    Jan. 18, 2007

Related U.S. Application Data

(63) Continuation-in-part of application No. 11/375,128, filed on Mar. 15, 2006, now abandoned, application No. 11/471,514, which is a continuation-in-part of application No. 11/375,033, filed on Mar. 15, 2006, now Pat. No. 7,785,883, which is a continuation-in-part of application No. 11/116,234, filed on Apr. 28, 2005, now Pat. No. 7,855,074.

(60) Provisional application No. 60/565,846, filed on Apr. 28, 2004, provisional application No. 60/643,175, filed on Jan. 13, 2005, provisional application No. 60/752,034, filed on Dec. 21, 2005.

(51) Int. Cl.
  C12N 5/0781    (2010.01)
  C12N 5/0783    (2010.01)
  C12N 5/0784    (2010.01)

(52) U.S. Cl. .......................... 435/347; 435/373; 435/395

(58) Field of Classification Search .................. 435/347, 435/373, 395
See application file for complete search history.

(56) References Cited

U.S. PATENT DOCUMENTS

| | | | |
|---|---|---|---|
| 5,008,116 A | 4/1991 | Cahn | |
| 5,160,490 A | 11/1992 | Naughton et al. | |
| 5,354,686 A | 10/1994 | Haberman | |
| 5,562,910 A | 10/1996 | Daynes et al. | |
| 5,725,856 A | 3/1998 | Hudziak et al. | |
| 5,739,001 A | 4/1998 | Brown et al. | |
| 5,750,329 A | 5/1998 | Quinn et al. | |
| 6,177,282 B1 | 1/2001 | McIntyre | |
| 6,274,378 B1 | 8/2001 | Steinman et al. | |
| 6,479,064 B1 | 11/2002 | Atala | |
| 6,541,225 B1 | 4/2003 | Li | |
| 6,835,550 B1 | 12/2004 | Estell et al. | |
| 2002/0155108 A1 | 10/2002 | Barbera-Guillem et al. | |
| 2003/0109042 A1 | 6/2003 | Wu et al. | |
| 2003/0147923 A1 | 8/2003 | Klaviniskis | |
| 2003/0199006 A1 | 10/2003 | Britz et al. | |
| 2003/0207287 A1 | 11/2003 | Short | |
| 2004/0009943 A1 | 1/2004 | Semple et al. | |
| 2004/0109876 A1 | 6/2004 | Yamamoto et al. | |
| 2004/0234510 A1* | 11/2004 | Mochitate ..................... 424/93.7 |
| 2005/0191743 A1* | 9/2005 | Wu et al. ....................... 435/366 |
| 2005/0229264 A1 | 10/2005 | Chang et al. | |
| 2005/0282148 A1 | 12/2005 | Warren et al. | |
| 2006/0078540 A1 | 4/2006 | Warren et al. | |
| 2006/0105454 A1 | 5/2006 | Son et al. ...................... 435/325 |
| 2006/0270029 A1 | 11/2006 | Warren et al. | |
| 2006/0275270 A1 | 12/2006 | Warren et al. | |
| 2007/0015136 A1 | 1/2007 | Sanchez-Schmitz et al. | |
| 2007/0141552 A1 | 6/2007 | Warren et al. | |
| 2007/0154956 A1 | 7/2007 | Warren et al. | |
| 2007/0178076 A1 | 8/2007 | Drake et al. | |
| 2007/0218054 A1 | 9/2007 | Sukumar et al. | |
| 2008/0008653 A1 | 1/2008 | Tew et al. | |
| 2009/0011455 A1 | 1/2009 | Warren et al. | |
| 2009/0104221 A1 | 4/2009 | El Shikh et al. | |
| 2009/0117581 A1 | 5/2009 | Warren et al. | |

FOREIGN PATENT DOCUMENTS

| | | |
|---|---|---|
| EP | 0 358 506 | 9/1989 |
| EP | 1013668 A1 | 6/2000 |
| EP | 1 437 147 | 9/2002 |
| EP | 1970444 A1 | 12/2006 |
| WO | 99/12972 | 3/1999 |
| WO | WO 99/15629 | 4/1999 |
| WO | WO 99/43788 | 9/1999 |
| WO | WO99/49319 | 9/1999 |
| WO | WO 03/041568 | 5/2003 |
| WO | WO 03/050271 | 6/2003 |
| WO | WO 2004/031361 | 4/2004 |
| WO | WO2004/101773 | 11/2004 |
| WO | 2005/013896 | 2/2005 |

(Continued)

OTHER PUBLICATIONS

Sarradell et al. (2003) Vet. Pathol., vol. 40, 395-404.*
Tan et al. (2005) J. Leuk. Biol., vol. 78, 319-324.*
Takeuchi et al. (2004) Clin. Canc. Res., vol. 10, 2351-2358.*
Katakai et al. (2004) J. Exp. Med., vol. 200(6), 783-795.*
Gunzer et al. (2000) Immunity, vol. 13, 323-332.*
John G. Tew et al., "Follicular Dendritic Cells and Presentation of Antigen and Costimulatory Signals to B Cells," Immunological Reviews (1997), vol. 156, pp. 39-52.
Akiko Furuyama et al., "Assembly of Basement Membrane in vitro by Cooperation Between Alveolar Epithelial Cells and Pulmonary Fibroblasts," Cell Structure and Function (1997), vol. 22, pp. 603-614.

(Continued)

Primary Examiner — Anne Marie S Wehbe
(74) Attorney, Agent, or Firm — Roylance, Abrams, Berdo & Goodman LLP

(57) ABSTRACT

The present invention relates to methods of constructing an integrated artificial immune system that comprises appropriate in vitro cellular and tissue constructs or their equivalents to mimic the normal tissues that interact with vaccines in mammals. The artificial immune system can be used to test the efficacy of vaccine candidates in vitro and thus, is useful to accelerate vaccine development and testing drug and chemical interactions with the immune system.

18 Claims, 20 Drawing Sheets

FOREIGN PATENT DOCUMENTS

| WO | 2005/072088 | 8/2005 |
| WO | WO 2005/104755 | 11/2005 |
| WO | WO 2007/075979 | 7/2007 |
| WO | 2007/108835 | 9/2007 |
| WO | WO 2007/106559 | 9/2007 |
| WO | WO 2007/146267 | 12/2007 |

OTHER PUBLICATIONS

Stephen F. Badylak et al., "*Small Intestinal Submucosa: A Substrate for in vitro Cell Growth*," J. Biomater. Sci. Polymer Edn. (1998), vol. 9, No. 8, pp. 863-878.

Shaoli Zhang et al., "*Growth Factors Secreted by Bronchial Epithelial Cells Control Myofibroblast Proliferation: An in vitro Co-culture Model of Airway Remodeling in Asthma*," Laboratory Investigation (1999), vol. 79, No. 4, pp. 395-405.

H. Garrett Thompson et al., "*A Three-dimensional in vitro Model of Angiogenesis in the Airway Mucosa*," Pulmonary Pharmacology & Therapeutics (2007), vol. 20, pp. 141-148.

M. Nakamura et al., "*Expression of Leptin in Two-layered Culture of Gastric Mucous Cells and Fibroblasts: Effect of Helicobacter pylori Attachment*," Aliment Pharmacol Ther. (2004), vol. 20, suppl. 1, pp. 125-130.

Martin N. Nakatsu et al., "*Angiogenic Sprouting and Capillary Lumen Formation Modeled by Human Umbilical Vein Endothelial Cells (HUVEC) in Fibrin Gels: The Role of Fibroblasts and Angiopoietin-1*," Microvascular Research (2003), vol. 66, pp. 102-112.

Per Brandtzaeg et al., "*Mucosal B Cells: Phenotypic Characteristics, Transcriptional, Regulation, and Homing Properties*," Immunological Reviews (2005), vol. 206, pp. 32-63.

Tarte et al., Leukemia, vol. 14, 2000, abstract p. 2182.

Kim et al., "*Three-Dimensional Tissue Culture Models in Cancer Biology*," Seminars in Cancer Biology, (2005), 15(5), pp. 365-377.

A. R. Neves, et al., "*Dendritic Cells Derived From Metastatic Cancer Vaccinated With Allogeneic Dendritic Cell-Autologous Tumor Cell Hybrids Express More CD86 and Induce Higher Levels of Interferon-Gamma in Mixed Lymphocyte Reactions*," Cancer Immunology and Immunotherapy, (2005), 54(1), pp. 61-66.

S. Büchele et al., "*Presentation of Tetanus Toxoid to Autologous T Cells by Dendritic Cells Generated From Human Blood. Improved Specificity With Dendritic Cells Generated Without Fetal Calf Serum*," Advances in Experimental Medicine and Biology, (1997), vol. 417, pp. 233-237.

Bai et al., "*Generation of Dendritic Cells From Human Bone Marrow Mononuclear Cells: Advantages From Clinical Applications in Comparison to Peripheral Blood Monocyte Derived Cells*," International Journal of Oncology, (2002), 20(2), pp. 247-253.

K. V. Bromelow et al., "*Whole Blood Assay for Assessment of the Mixed Lymphocyte Reaction*," Journal of Immunological Methods, (2001), 247(1-2), pp. 1-8.

M. H. Kosco et al., "*Follicular Dendritic Cells and Germinal Center Formation In-Vitro*," Accessory Cells in HIV and Other Retroviral Infections: Morphological and Functional Aspects; Workshop on Morphological and Functional Aspects of Accessory Cells in Tretroviral Infections, Hamberg, Germany, 23-24, p. 44-49 (1991).

M. H. Kosco et al., "*Folicular Dendritic Cell-Dependent B-Cell Proliferation and in Vitro Germinal Center*," Lymphatic Tissues In Vivo Immune Responses, (1991), pp. 687-690.

O. Soderberg et al., "*The Human Follicular Dendritic Cell Line FDC-1 Binds Immune Complexes and Promotes Somatic Hypermutation*," Blood, (2001), 98(11 part 2), pp. 40b.

R. Tsunoda et al., "*Human Follicular Dendritic Cells In Vitro and Follicular Dendritic-Cell-Like Cells*," Cell and Tissue Research, (1997), 288(2), pp. 381-389.

R. Tsunoda et al., "*Follicular Dendritic Cells In Vitro Modulate the Expression of Fas and Bcl-2 on Germinal Center B Cells*," Cell and Tissue Research, (2000), 299(3), pp. 395-402.

J. G. Tew et al., "*Follicular Dendritic Cells As Accessory Cells*," Immunological Reviews, (1990), No. 117, pp. 185-211.

M. H. Kosco et al., "*Follicular Dendritic Cell-Dependent Adhesion and Proliferation of B Cells In Vitro*," Journal of Immunology, (1992), 148(8), pp. 2331-2339.

Y. Wu et al., "*Influence of Follicular Dendritic Cells and Primed T Cells on Somatic Hypermutation in In Vitro Germinal Centers*," Journal of Immunology, (2006), 176(suppl. S), pp. S235-S236.

M. El Shikh et al., "*Follicular Dendritic Cells Stimulated by Collagen Type I Develop Dendrites and Networks In Vitro*," Cell and Tissue Research, (2007), 329(1), pp. 81-89.

R. Seguin et al., "*Human Brain Endothelial Cells Supply Support for Monocyte Immunoregulartory Functions*," Journal of Neuroimmunology, (2003), 135(1-2), pp. 96-106.

S Levenberg et al., "*Advances in Tissue Engineering*," Current Topics in Developmental Biology, (2004), vol. 61, pp. 113-134.

P. Manna et al., "Differentiation and Functional Maturation of Human CD14<+> Adherent Peripheral Blood Monocytes by Xenogeneic Endothelial Cells: Up-Regulation of Costimulation Cytokine Generation, and Toll-Like Receptors," Transplantation, (2002), 74(2), pp. 243-252.

International Search Report for PCT/US05/14444, dated Mar. 21, 2008.

International Search Report for PCT/US06/43563, dated Nov. 29, 2007.

International Search Report for PCT/US06/43712, dated Aug. 8, 2007.

International Search Report for PCT/US07/006532, dated Feb. 18, 2008.

International Search Report for PCT/US07/006571, dated Sep. 21, 2007.

Partial International Search for PCT/US07/013745, dated Jan. 28, 2008.

International Search Report for PCT/US07/013871, dated Mar. 3, 2008.

International Search Report for PCT/US06/049128, dated Jun. 12, 2007.

Benbrook et al., "Organotypic cultures represent tumor microenvironment for drug testing," Drug Discovery Today: Disease Models, 3(2), pp. 143-148 (2005).

International Search for PCT/US07/013745, dated Apr. 18, 2008.

U.S. Appl. No. 11/453,046, filed Jun. 15, 2006, Warren et al.

U.S. Appl. No. 11/453,003, filed Jun. 15, 2006, Warren et al.

Suematsu, et al., "Generation of a Synthetic Lymphoid Tissue-Like Organoid in Mice", Nature Biotechnology, vol. 22, No. 12. pp. 1539-1545 (Dec. 2004).

Randolph, et al., "Role of Tissue Factor in Adhesion of Mononuclear Phagocytes to and Trafficking Through Endothelium in Vitro", Blood, vol. 92, pp. 4167-4177 (1998).

Randolph, et al., "Differentiation of Monocytes into Dendritic Cells in a Model of Transendothelial Trafficking", Science, vol. 282, pp. 480-483 (1998).

Randolph, et al., "A Physiologic Function for p-Glycoprotein (MDR-1) During the Migration of Dendritic Cells from Skin Via Afferent Lymphatic Vessels", Proc. Natl. Acad. Sci., vol. 95, pp. 6924-2929 (1998).

Randolph, et al.. "The CD16(+) (FcγRIII(+)) Subset of Human Monocytes Preferentially Becomes Migratory Dendritic Cells in a Model Tissue Setting", J. Exp. Med., vol. 196, No. 4, pp. 517-527 (2002).

Randolph, et al., "Mononuclear Phagocytes Egress from an In Vitro Model of the Vascular Wall by Migrating Across Endothelium in the Basal to Apical Direction: Role of Intercellular Adhesion Molecule 1 and the CD11/CD18 Integrins", J. Exp. Med., vol. 183, pp. 451-462 (1996).

Randolph, et al., "A Soluble Gradient of Endogenous Monocyte Chemoattractant Protein-1 Promotes the Transendothelial Migration of Monocytes In Vitro", The Journal of Immunology, vol. 155, pp. 3610-3618 (1995).

Furie, et al., "Migration of Neutrophils Across Endothelial Monolayers is Stimulated by Treatment of the Monolayers with Interleukin-1 or Tumor Necrosis Factor-Alpha", The Journal of Immunology, vol. 143, pp. 3309-3317 (1989).

Robbiani, et al., "The Leukotriene C4 Transporter MRPI Regulates CCL19 (MIP-3β, ELC)-Dependent Mobilization of Dendritic Cells to Lymph Nodes", Cell, vol. 103, pp. 757-768 (2000).

Podgrabinska, et al., "Molecular Characterization of Lymphatic Endothelial Cells", Proc. Natl. Acad. Sci. U.S.A., vol. 99, No. 25, pp. 16069-16074 (2002).

Berman, et al., "Roles of Platelet/Endothelial Cell Adhesion Molecule-1 (PECAM-1, CD31) in Natural Killer Cell Transendothelial Migration and Beta 2 Integrin Activation", The Journal of Immunology, vol. 156, pp. 1515-1524 (1996).

Gergel, et al., "Activation of Endothelium by *Borrelia burgdorferi* In Vitro Enhances Transmigration of Specific Subsets of T Lymphocytes", Infection and Immunity, vol. 69, pp. 2190-2197 (2001).

Qu, et al., "Autocrine Type I IFN and Contact with Endothelium Promote the Presentation of Influenza a Virus by Monocyte-Derived APC", The Journal of Immunology, vol. 170, pp. 1010-1018 (2003).

Mellman, et al., "Dendritic Cells: Specialized and Regulated Antigen Processing Machines", Cell, vol. 106, pp. 255-258 (2001).

Lukas, et al., "Human Cutaneous Dendritic Cells Migrate Through Dermal Lymphatic Vessels in a Skin Organ Culture Model", The Journal of Investigative Dermatology, vol. 106, pp. 1293-1299 (1996).

Fransson, et al., "Culture of Human Epidermal Langerhans Cells in a Skin Equivalent", British Journal of Dermatology, vol. 139, pp. 598-604 (1998).

Banchereau, et al., "Immunobiology of Dendritic Cells", Annu. Rev. Immunol., vol. 18, pp. 767-811 (2000).

Butcher, et al., "Lymphocyte Trafficking and Regional Immunity", Advances in Immunology, vol. 72, pp. 209-253 (1999).

Sprent, et al., "Antigen-Induced Selective Recruitment of Circulating Lymphocytes", Cellular Immunology, vol. 2, pp. 171-181 (1971).

Garside, et al., "Visualization of Specific B and T Lumphocyte Interactions in the Lymph Node", Science, vol. 281, pp. 96-99 (1998).

Jenkins, et al., "In Vivo Activation of Antigen-Specific CD4 T Cells", Annu. Rev. Immunol., vol. 19, pp. 23-45 (2001).

Kaldjian, et al., "Spatial and Molecular Organization of Lymph Node T Cell Cortex: A Labyrinthine Cavity Bounded by an Epithelium-Like Monolayer of Fibroblastic Reticular Cells Anchored to Basement Membrane-like Extracellular Matrix", International Immunology, vol. 13, pp. 1243-1253 (2001).

Gretz, et al., "Sophisticated Strategies for Information Encounter in the Lymph Node: The Reticular Network as a Conduit of Soluble Information and a Highway for Cell Traffic", The Journal of Immunology, vol. 157, pp. 495-499 (1996).

Van Den Berg, et al., "Localization of β 1 Integrins and Their Extracellular Ligands in Human Lymphoid Tissues", American Journal of Pathology, vol. 143, pp. 1098-1110 (1993).

Gretz, et al., "Lymph-borne Chemokines and Other Low Molecular Weight Molecules Reach High Endothelial Venules Via Specialized Conduits While a Functional Barrier Limits Access to the Lymphocyte Microenvironments in Lymph Node Cortex", The Journal of Experimental Medicine, vol. 192, pp. 1425-1439 (2000).

Stuart, et al., "The Human Reticular Cell: Morphology and Cytochemistry", J. Pathol, vol. 103, pp. 41-47 (1971).

Crivellato, et al., "Stromal Cell Organisation in the Mouse Lymph Node. A Light and Electron Microscopic Investigation Using the Zinc Iodide-Osmium Technique", J. Anat., vol. 190, pp. 85-92 (1997).

Gretz, et al., "Cords, Channels, Corridors and Conduits: Critical Architectural Elements Facilitating Cell Interactions in the Lymph Node Cortex", Immunological Reviews, vol. 156, pp. 11-24 (1997).

Friedl, et al., "CD4+ T Lymphocytes Migrating in Three-Dimensional Collagen Lattices Lack Focal Adhesions and Utilize Beta I Integrin-Independent Strategies for Polarization, Interaction with Collagen Fibers and Locomotion", Eur. J. Immunol., vol. 28, pp. 2331-2343 (1998).

Forster, et al., "CCR7 Coordinates the Primary Immune Response by Establishing Functional Microenvironments in Secondary Lymphoid Organs", Cell., vol. 99, pp. 23-33 (1999).

Gunn, et al., "Mice Lacking Expression of Secondary Lymphoid Organ Chemokine Have Defects in Lymphocyte Homing and Dentritic Cell Localization", J. Exp. Med., vol. 189, pp. 451-460 (1999).

Junt, et al., "Antiviral Immune Responses in the Absence of Organized Lymphoid T Cell Zones in *plt/plt* Mice", The Journal of Immunology, vol. 168, pp. 6032-6040 (2002).

Mori, et al., "Mice Lacking Expression of the Chemokines CCL21-ser and CCL19 (plt Mice) Demonstrate Delayed but Enhanced T Cell Immune Responses", J. Exp. Med., vol. 193, No. 2, pp. 207-217 (2001).

Gunzer, et al., "Antigen Presentation in Extracellular Matrix: Interactions of T Cells with Dendritic Cells are Dynamic, Short Lived, and Sequential", Immunity, vol. 13, pp. 323-332 (2000).

Miller, et al., "Two-Photon Imaging of Lymphocyte Motility and Antigen Response in Intact Lymph Node", Science, vol. 296, pp. 1869-1873 (2002).

Stoll, et al., "Dynamic Imaging of T Cell-Dendritic Cell Interactions in Lymph Nodes", Science, vol. 296, pp. 1873-1876 (2002).

Baumgarth, "A Two-Phase Model of B-Cell Activation", Immunological Review, vol. 176, pp. 171-180 (2000).

Futcher, et al., "B-Cell Activation Versus Tolerance—The Central Role of Immunoglobulin Receptor Engagement and T-Cell Help", Int. Rev. Immunol., vol. 15, pp. 33-52 (1997).

Parker, "T Cell-Dependent B Cell Activation", Annu. Rev. Immunol., vol. 11. pp. 331-360 (1993).

Kosco-Vilbois, "Are Follicular Dendritic Cells Really Good for Nothing", Nature Reviews Immunology, vol. 3, pp. 764-769 (2003).

Skibinski, et al., "Enhancement of Terminal B Lymphocyte Differentiation in Vitro by Fibroblast-Like Stromal Cells from Human Spleen", Eur. J. Immunol., vol. 28, pp. 3940-3948 (1998).

Dubois, et al., "Dendritic Cells Enhance Growth and Differentiation of CD40-Activated B Lymphocytes", J. Exp. Med., vol. 185, pp. 941-951 (1997).

Cyster, et al., "Follicular Stromal Cells and Lymphocyte Homing to Follicles", Immunological Reviews, vol. 176, pp. 181-193 (2000).

Matsumoto, et al., "Affinity Maturation Without Germinal Centres in Lymphotoxin-α-Deficient Mice", Nature, vol. 382, pp. 462-466 (1996).

Pasparakis, et al., "Immune and Inflammatory Responses in TNFα Deficient Mice: A Critical Requirement for TNFα in the Formation of Primary B Cell Follicles, Follicular Dendritic Cell Networks and Germinal Centers, and in the Maturation of the Humoral Immune Response", J. Exp. Med., vol. 184, pp. 1397-1411 (1996).

Toyama, et al., "Memory B Cells Without Somatic Hypermutation are Generated from Bcl 6 Deficient B Cells", Immunity, vol. 17, pp. 329-339 (2002).

Galibert, et al., "CD40 and B Cell Antigen Receptor Dual Triggering of Resting B Lymphocytes Turns on a Partial Germinal Center Phenotype", J. Exp. Med., vol. 183, pp. 77-85 (1996).

Razanajaona, et al., "In Vitro Triggering of Somatic Mutation in Human Naïve B Cells", The Journal of Immunology, vol. 159, pp. 3347-3353 (1997).

Phillips, et al., "Activation of Pertussis Toxin-Sensitive CXCL12 (SDF-1) Receptors Mediates Transendothelial Migration of T Lymphocytes Across Lymph Node High Endothelial Cells", Eur. J. Immunol., vol. 32, pp. 837-847 (2002).

Rot, "In Situ Binding Assay for Studying Chemokine Interactions with Endothelial Cells", Journal of Immunological Methods, vol. 273, pp. 63-71 (2003).

Irvine, et al., "Nanoscale Clustering of RGD Peptides at Surfaces Using Comb Polymers. 1. Synthesis and Characterization of Comb Thin Films", Biomacromolecules, vol. 2, pp. 85-94 (2001).

West, et al., "Polymeric Biomaterials with Degradation Sites for Proteases Involved in Cell Migration", Macromolecules, vol. 32, pp. 241-244 (1999).

Bogdan, et al., "Fibroblasts as Host Cells in Latent Leishmaniosis", J. Exp. Med., vol. 191, pp. 2121-2129 (2000).

Castro, et al., "Spleen-Derived Stromal Cells. Adhesion Molecules Expression and Lymphocyte Adhesion to Reticular Cells", Eur. J. Cell. Biol., vol. 74, 321-328 (1997).

Skibinski, et al., "The Role of Hepatocyte Growth Factor and Its Receptor *c-met* in Interactions Between Lymphocytes and Stromal Cells in Secondary Human Lymphoid Organs", Immunology, vol. 102, pp. 506-514 (2001).

LeBedis, et al., "Peripheral Lymph Node Stromal Cells Can Promote Growth and Tumorigenicity of Breast Carcinoma Cells Through the Release of IGF-I and EGF", Int. J. Cancer, vol. 100, pp. 2-8 (2002).

Ruco, et al., "Expression and Cell Distribution of the Intercellular Adhesion Molecule, Vascular Cell Adhesion Molecule, Endothelial Leukocyte Adhesion Molecule, and Endothelial Cell Adhesion Molecule (CD31) in Reactive Human Lymph Nodes and in Hodgkin's Disease", American Journal of Pathology, vol. 140, pp. 1337-1344 (1992).

Cyster, "Chemokines and the Homing of Dendritic Cells to the T Cell Areas of Lymphoid Organs", J. Exp. Med. vol. 189, No. 3, pp. 447-450 (1999).

Ansel, et al., "A Chemokine-Driven Positive Feedback Loop Organizes Lymphoid Follicles", Nature, vol. 406, pp. 309-314 (2000).

Mebius, "Organogenesis of Lymphoid Tissues", Nat. Rev. Immunol, vol. 3, pp. 292-303 (2003).

Poznansky, et al., "Efficient Generation of Human T Cells From a Tissue-Engineered Thymic Organoid", Nature Biotechnology, vol. 18, pp. 729-734 (2000).

Safarik, et al., "Use of Magnetic Techniques for the Isolation of Cells", Journal of Chromatography B, vol. 722, pp. 33-53 (1999).

Dynal (Norway): http://www.invitrogen.com/.

Agowa GMBH (Germany): http://agowade/contentsframes/magneticseparation/particle.html.

Chen, et al., "A Film Tension Theory of Phagocytosis", Journal of Colloid and Interface Science, vol. 190, pp. 118-133 (1997).

Banchereau, et al., "Dendritic Cells and the Control of Immunity", Nature, vol. 392, pp. 245-252 (1998).

Kabashima, et al., "Prostaglandin $E_2$-EP4 Signaling Initiates Skin Immune Responses by Promoting Migration and Maturation of Langerhans Cells", Nature Medicine, vol. 9, pp. 744-749 (2003).

Denkbas, et al., "Magnetic Chotosan Microspheres: Preparation and Characterization", Reactive & Functional Polymers, vol. 50, pp. 225-232 (2002).

Larsson, et al., "Requirement of Mature Dendritic Cells for Efficient Activation of Influenza A-Specific Memory CD8 + T Cells", The Journal of Immunology, vol. 165, pp. 1182-1190 (2000).

Danke, et al., "HLA Class II-Restricted CD4+ T Cell Responses Directed Against Influenza Viral Antigens Postinfluenza Vaccination", The Journal of Immunology, vol. 171, pp. 3163-3169 (2003).

Hasbold, et al., "Quantitative Analysis of Lymphocyte Differentiation and Proliferation in Vitro Using CarboxyFluorescein Diacetate Succinimidyl Ester", Immunology and Cell Biology, vol. 77, pp. 516-522 (1999).

Luk, et al., "Rapid and Sensitive Detection of *Salmonella* (O:6,7) by Immunomagnetic Monoclonal Antibody-Based Assays", Journal of Immunological Methods, vol. 137, pp. 1-8 (1991).

Gundersen, et al., "Magnetic Bead Antigen Capture Enzyme-Linked Immunoassay in Microtitre Trays for Rapid Detection of Schistosomal Circulating Anodic Antigen", Journal of Immunological Methods, vol. 148, pp. 1-8 (1992).

Chou, et al., "The Detection of the HLA-B27 Antigen by Immunomagnetic Separation and Enzyme-Linked Immunosorbent Assay-Comparison with a Flow Cytometric Procedure", Journal of Immunological Methods, vol. 255, pp. 15-22 (2001).

Kourilov, et al., "Magnetic-Bead Enzyme-Linked Immunosorbent Assay Verifies Adsorption of Ligand and Epitope Accessibility", Analytical Biochemistry, vol. 311, pp. 166-170 (2002).

http://www.xcyte.com.

Protocol for anti-CD3 Activation of T-Cells from E-Bioscience (San Diego, CA): http://www.ebioscience..com/ebioscience/appls/AC145.htm.

Kadowaki, et al., "Subsets of Human Dendritic Cell Precursors Express Different Toll-Like Receptors and Respond to Different Microbial Antigens", J. Exp. Med. vol. 194, No. 6, pp. 863-869 (2001).

Sieben, et al., "Comparison of Different Particles and Methods for Magnetic Isolation of Circulating Tumor Cells", Journal of Magnetism and Magnetic Materials, vol. 225, pp. 175-179 (2001).

Regnier, et al., "Integration of Langerhans Cells into a Pigmented Reconstructed Human Epidermis", The Journal of Investigative Dermatology, vol. 109, No. 4, pp. 510-512 (1997).

Abas, et al., "J.S. Cellular and Molecular Immunology", W.B. Sanders Co., New York, NY (2000).

Banchereau, et al., "Dendritic Cells and the Control of Immunity", Nature, vol. 392, pp. 245-252 (1998).

H.-J. Kim et al, Establishment of Early Lymphoid Organ Infrastructure in Transplanted Tumors Mediated by Local Production of Lymphotoxin α and in Combined Absence of Functional B and T Cells. In J. of Immunology, vol. 172:4037-4047 (2004).

Portner, R et al, Chapter 2: An Overview on Bioreactor Design, Prototyping, and Process Control for Reproducible Three-Dimensional Tissue Culture. In Drug Testing In Vitro: Breakthrough Cell Cultur Technology. Eds. U. Marx and V. Sandig 2006: Wiley-VCH, pp. 65-69.

Okamoto et al, Artificial Lymph Nodes Induce Potent Secondary Immune Response in Naïve and Immunodeficient Mice. J. Clin. Invest. Apr. 2007, vol. 117, No. 4, pp. 997-1007.

Edelman et al, A Cultureal Renaissance: In Vitro Cell Biology Embraces Three-Dimensional Context. Exp Neurol. 2005, vol. 192, pp. 1-6.

Birkness et al., An In Vitro Tissue Culture Bilayer Model to Examine Early Events in Mycobacterium Tuberculosis Infection, *Infection and Immunity*, Feb. 1999, p. 653-658, vol. 67, No. 2.

Birkness et al., A Tissue Culture Bilayer Model to Study the Passage of Neisseria Meningitidis, *Infection and Immunity*, Feb. 1995, p. 402-409, vol. 63, No. 2.

Weppler et al., Modulation of Endotoxin-Induced Neutrophil Transendothelial Migration by Alveolar Epithelium in a Defined Bilayer Model, *Experimental Lung Research* 32:10, 455-482 (2006).

International Search Report—PCT/US2007/08379.

International Search Report—PCT/US2008/056720.

Sarradell et al. (2003) *Vet. Pathol.*, 40, 395-404.

Oehler et al. (2000) *Ann. Hematol.*, 79, 355-362.

Buehler et al. (2003) *Vaccine*, 21, 877-882.

Dubey et al. (2005) *J. Clin. Endocrin & Met.*, 90, 247-255.

Roos et al. (2005) *Expert Opin. Drug Metab. Toxicol.* 1, 187-202.

Boni et al. (2006) *Eur. J. Immunol.* 36, 3157-3166.

Caux et al. (1995) *J. Immunol.* 155, 5427-5435.

Moser et al. (2000) *Nature Immunol.* 1, 199-205.

Tan et al. (2005) *J. Leuk. Biol.* 78, 319-324.

Aydar et al. (2005)*J. Immunol.* 174, 5358-5366.

Tew et al. (2001) *Trends Immunol.* 22, 361-367.

Wu et al. (2008)*J. Immunol.* 180, 281-290.

Cayeux et al. (1999) *Eur. J. Immunol.* 29, 225-234.

Santini et al. (2000) *J. Exp. Med.* 191, 1777-1788.

International Search Report—PCT/US08/70107.

International Search Report—PCT/US06/048959.

International Search Report—PCT/US07/014826.

International Search Report—PCT/US08/69172, dated Mar. 25, 2009.

International Search Report—PCT/US08/70107, dated Mar. 13, 2009.

Warren, W., The Front-End of Vaccine Manufacturing: Getting Good Candidates from the Get-Go. Workshop on Science and Technology in North American Rapid Vaccine Manufacturing, Jan. 26, 2007.

Hashimoto, K., et al., Direct Observation and Analysis of Spatiotemporal Dynamics of Individual Living Monocyte During Transendothelial Migration. Atherosclerosis 177(1):19-27 (Nov. 2004).

Hashimoto, K., et al., Direct Observation and Analysis of Spatiotemporal Dynamics of Individual Living Monocyte During Transendothelial Migration. Collection of Papers from 16th Bioengineering Conference, Jan. 21, 2004, pp. 13-14.

Higbee, R., et al., An Immunologic Model for Rapid Vaccine Assessment—A Clinical Trial in a Test Tube. ALTA 37, Suppl. 1, 19-27 (2009).

Grouard et al., Regulation of Human B Cell Activation by Follicular Dendritic Cell and T Cell Signals, Curr. Topic Microbiol. Immunol. 201:105-117 (1995).

Inaba et al., Clustering of Dendritic Cells, Helper T Lymphocytes, and Histocompatible B Cells During Primary Antibody Response in vitro, J. Exp. Med. 160:858-876 (1984).

Caux et al., Functional CD40 on B Lymphocytes and Dendritic Cells, Res. Immunol. 145:235-239 (1994).

Dubois et al., J. Leukocyte Biology, 1999, v.66, p. 224-230.

Gansuvd et al., Human Immunol., 2003, v.64, p. 427-439.

Clayton et al., Clin. Exp. Immunol., 2003, v.132, p. 174-179.

D'Amico et al., Blood 92:207-214 (1998).

Simmingskoeld et al., Scand. J. Immunol. 7:233-238 (1978).

Transwell® Permeable Supports Selection and Use Guide, Corning Corp., pp. 1-12 (2009).

Khademhosseini et al., "Microscale Technologies for Tissue Engineering and Biology," Proc. Natl. Acad. Sci. USA, vol. 103, pp. 2480-2487 (2006).

* cited by examiner

Figure 1. The state of the DCs can dictate their migration behavior.
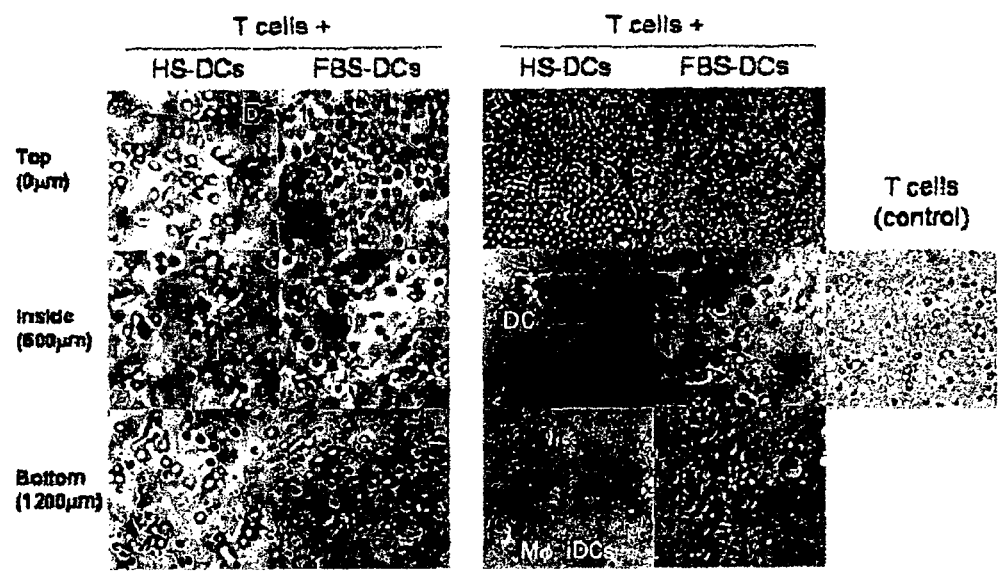

Figure 2. Mature DCs lead to T cell proliferation in a collagen layer.
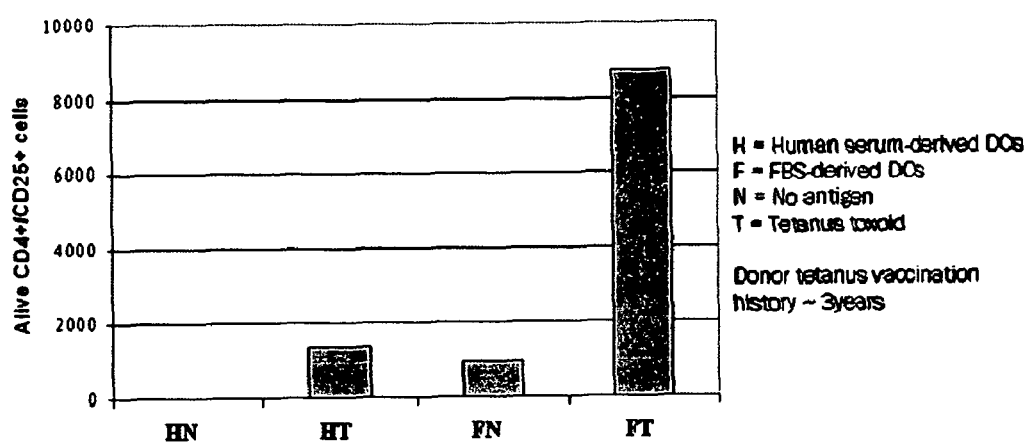

Figure 3. Detection of OT-II reporter T cell responses.
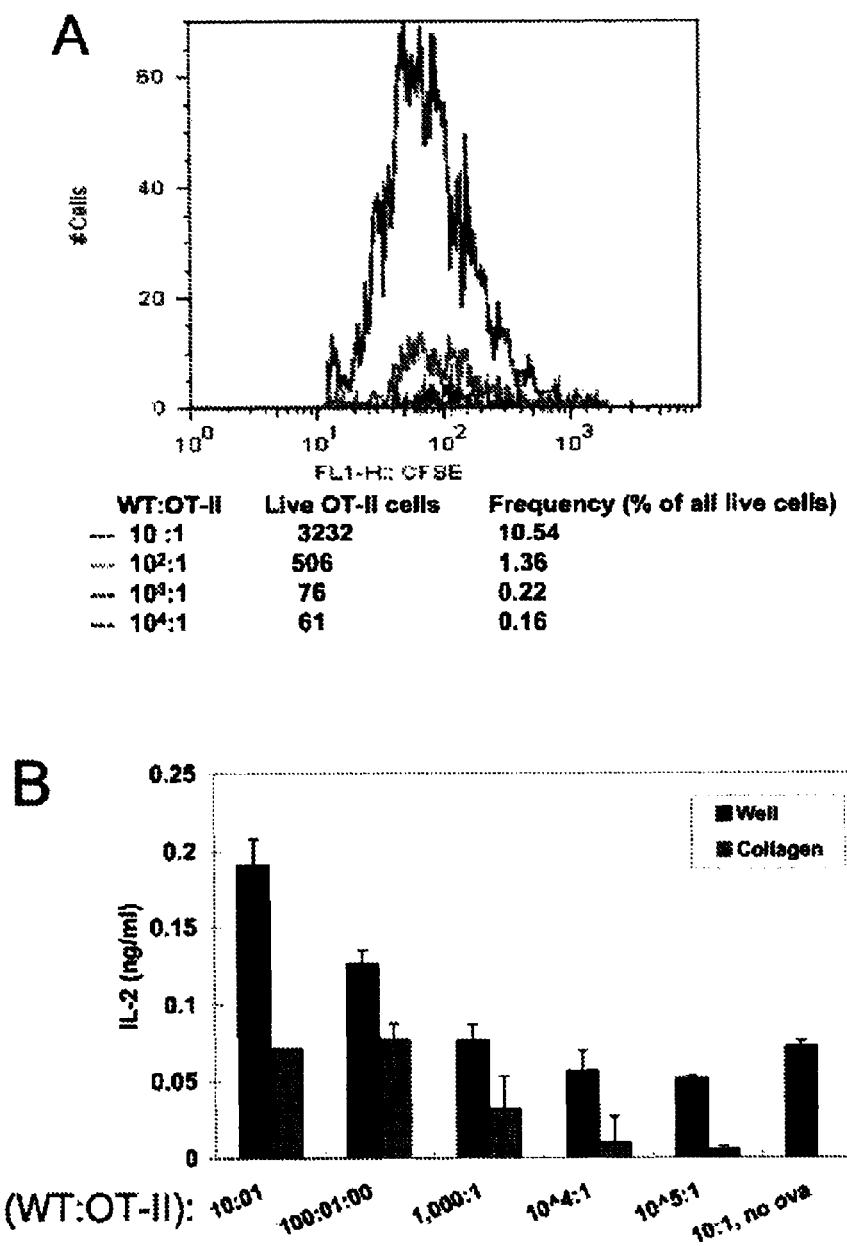

Figure 4. A method to enhance the expansion of rare T cells *in vitro*: use of chemokine CCL21.
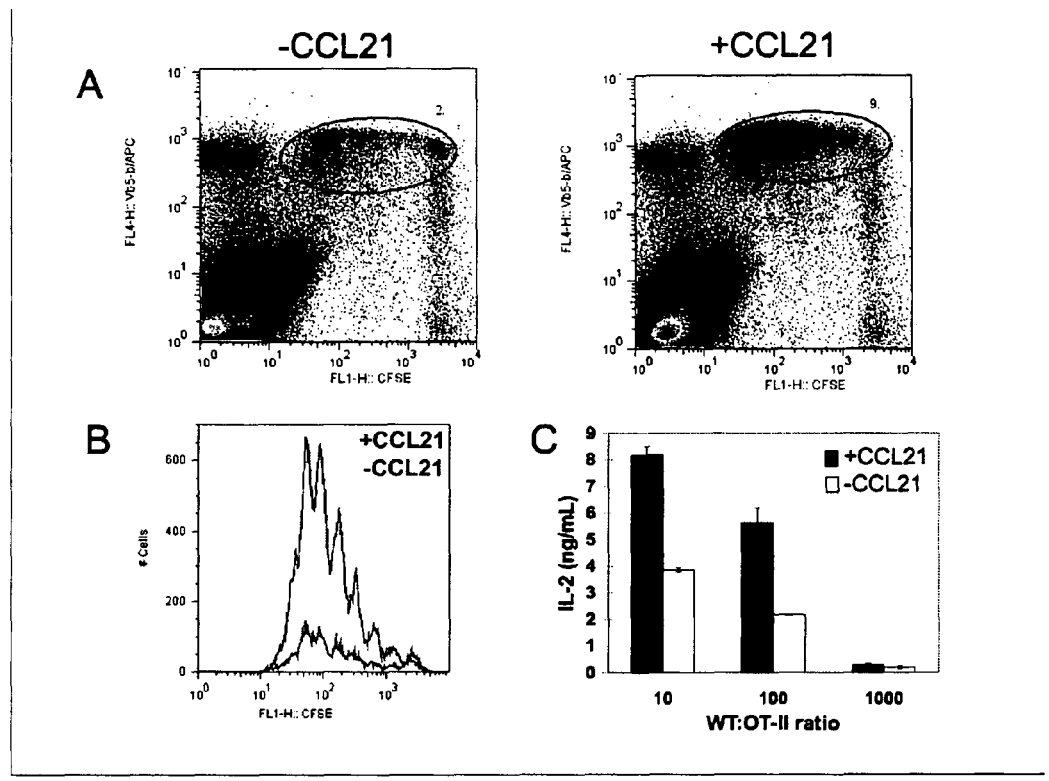

Figure 5. ECM production by BLS4 lymph node stromal cells.
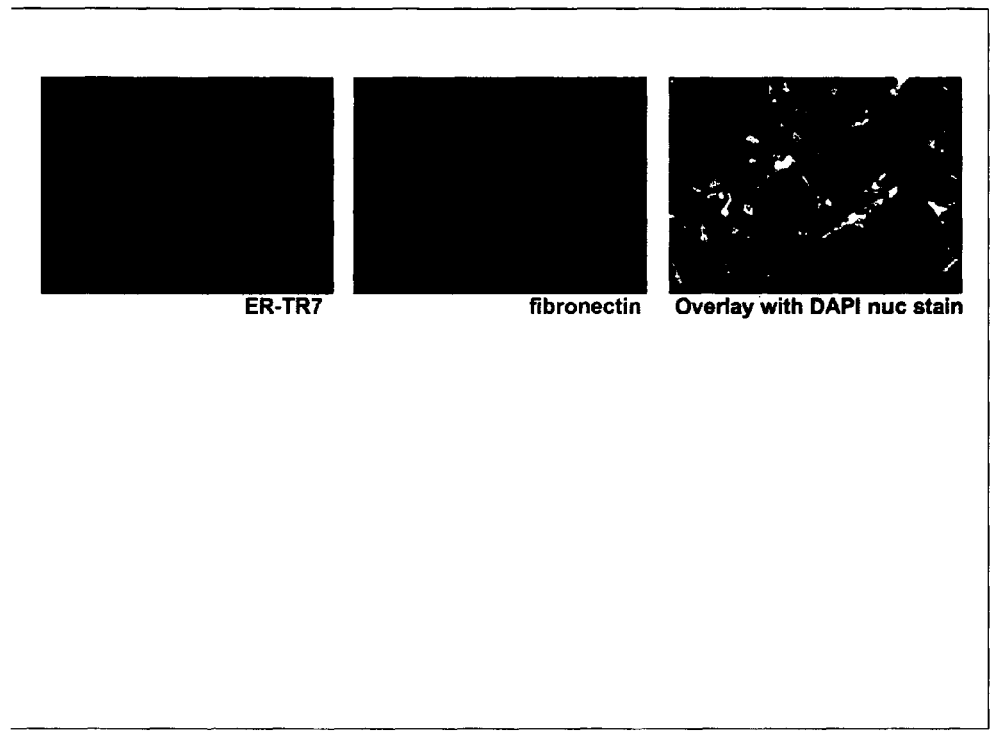

Figure 6. Effects of BLS4 stromal cells on lymphocyte survival.
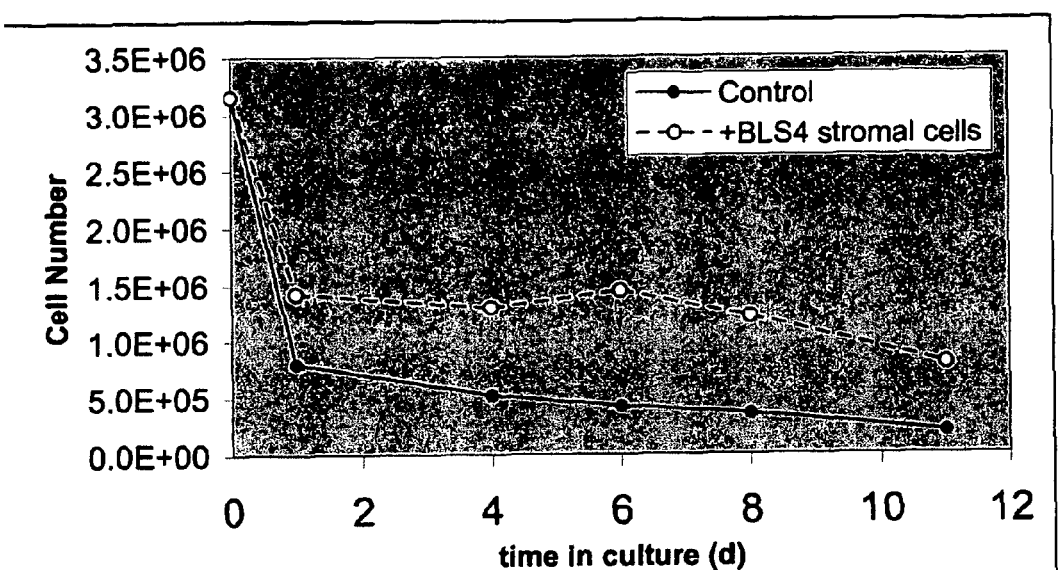

Figure 7. The ratio of immature to mature dendritic cells present in T-DC co-cultures impacts T cell proliferation and T cell survival.
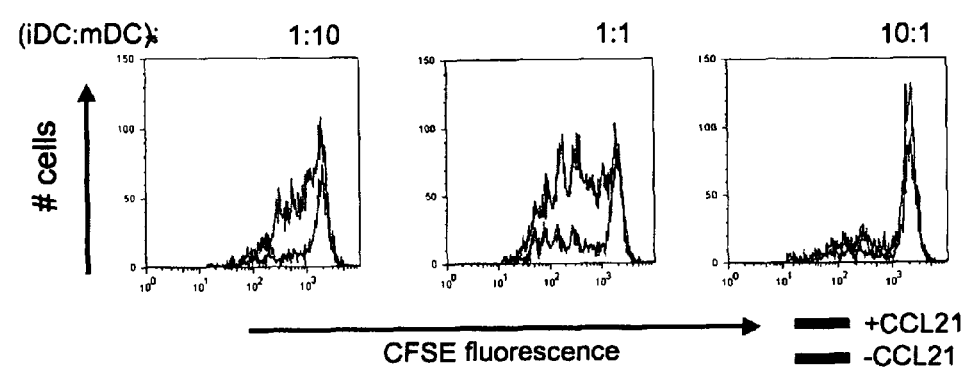

Figure 8. BLS4 stromal cells form reticular networks in protein-conjugated inverse opal scaffolds.
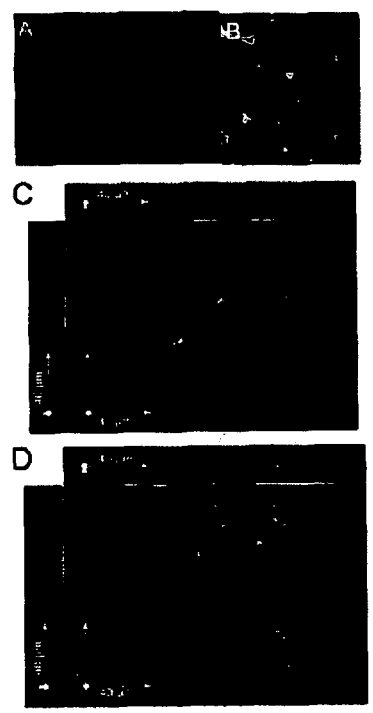

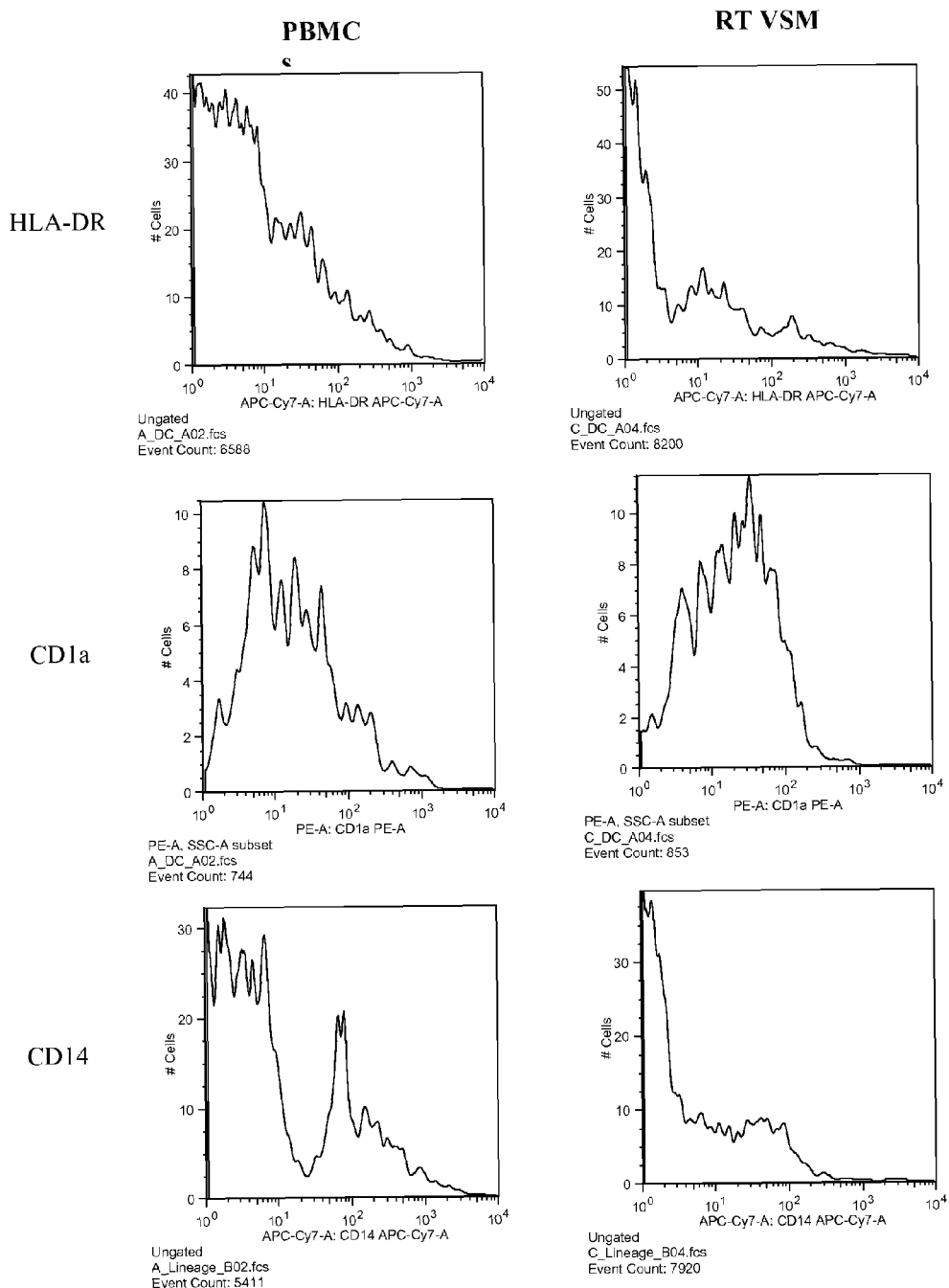
Figure 9A. Immature population of the RT-DCs from the VSM (membrane) or the VSC (cushion)

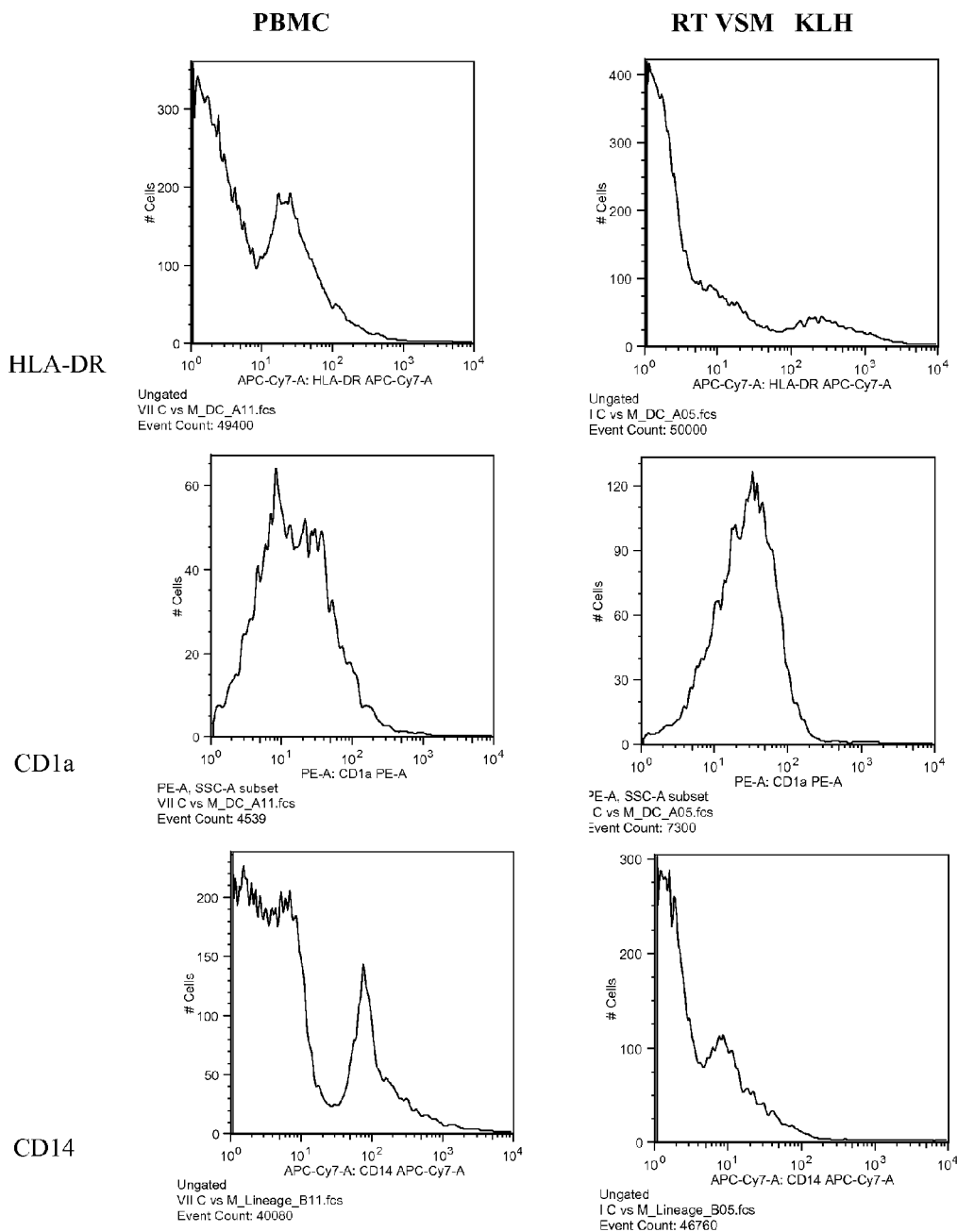
Figure 10A. After maturation with *Candida albicans*/tetanus toxoid/KLH antigens and TNFα

ARTIFICIAL LYMPHOID TISSUE EQUIVALENT

CROSS REFERENCE TO RELATED CASES

This application is a continuation-in-part of U.S. application Ser. No. 11/375,128, filed on Mar. 15, 2006 now abandoned, and published as U.S. Publication No. 2006/0275270, which is a continuation-in-part of U.S. application Ser. No. 11/116,234, filed Apr. 28, 2005 now U.S. Pat. No. 7,855,074, and published as U.S. Publication No. 2005/0282148, which claims the benefit of priority of U.S. Provisional Application Ser. No. 60/565,846, filed Apr. 28, 2004, and U.S. Provisional Application Ser. No. 60/643,175, filed Jan. 13, 2005. This application is also a continuation-in-part of U.S. application Ser. No. 11/375,033, filed on Mar. 15, 2006 now U.S. Pat. No. 7,785,883, and published as U.S. Publication No. 2006/0270029, which is a continuation-in-part of U.S. application Ser. No. 11/116,234, filed Apr. 28, 2005 now U.S. Pat. No. 7,855,074, which claims the benefit of priority of U.S. Provisional Application Ser. No. 60/565,846, filed Apr. 28, 2004, and U.S. Provisional Application Ser. No. 60/643,175, filed Jan. 13, 2005. This application also claims the benefit of priority of U.S. Provisional Application Ser. No. 60/752,034, filed Dec. 21, 2005. This application further claims the benefit of priority of International Application No. PCT/US2005/014444, filed Apr. 28, 2005. Each of these applications is hereby incorporated by reference in their entirety.

STATEMENT REGARDING FEDERALLY SPONSORED RESEARCH

This invention was made with government support under contract number NBCHC060058, awarded by the Defense Advanced Research Projects Agency, issued by the U.S. Army Medical Research Acquisition Activity, and administered by the U.S. Department of the Interior-National Business Center. The government has certain rights in the invention.

BACKGROUND OF THE INVENTION

1. Field of the Invention

The present invention is directed to a method for constructing an integrated artificial human tissue construct system and, in particular, construction of an integrated human immune system for in vitro testing of vaccines, adjuvants, immunotherapy candidates, cosmetics, drugs, biologics, and other chemicals. The artificial immune system of the present invention is useful for assessing the interaction of substances with the immune system, and thus can be used to accelerate and improve the accuracy and predictability of, for example, vaccine, drug, biologic, immunotherapy, cosmetic, and chemical development.

2. Background of the Technology

Despite the advent and promise of recent technologies, including combinatorial chemistry, high-throughput screening, genomics, and proteomics, the number of new drugs and vaccines reaching the market has not increased. In fact, the attrition rate within drug discovery programs exceeds 90%.

The introduction of these new (and expensive) technologies has not reduced the lost opportunity costs associated with immunotherapy development; rather, these costs have increased. It is now estimated that almost $1 billion is required to bring a new drug to the market.

The development and biological testing of human vaccines has traditionally relied on small animal models (e.g., mouse and rabbit models) and then non-human primate models. However, such small animal models are expensive and non-human primate models are both expensive and precious. Furthermore, there are many issues regarding the value of such animal studies in predicting outcomes in human studies.

A major problem remains the translation from test systems (animal or 2-dimensional (2D) cell culture) to human immunology. Successful transfer between traditional testing systems and human biology requires an intricate understanding of disease pathogenesis and immunological responses at all levels.

The body's distributed immune system can be roughly divided into four distinct compartments: tissues and blood, mucosal tissues, body cavities, and skin. Because of ease of study, most is known about the tissue and blood compartment and its lymphoid tissues, the spleen and lymph nodes.

The largest compartment is the MALT (mucosa-associated lymphoid tissue). Mucosal surfaces serve a wide range of functions, including exchange of gases (lungs), nutrient transport (digestive tract), sensory surfaces (nose, mouth, throat), and reproductive signals.

Mucosal immunity is important for several reasons. First, the vast majority of human pathogens, including many of the leading infectious disease killers, initiate infections at mucosal surfaces, the largest routes of entry into the body. Additionally, stimulation of a mucosal immune response can result in production of protective B and T cells in both mucosal and systemic environments, so that infections are stopped or significantly hindered before they enter the rest of body. Significantly, bioterrorism relies on entry of agents through mucosal surfaces, where pathogens or toxins are primarily encountered, not as injections.

Because of its large surface area and exposure to the outside world, the mucosal system is also more vulnerable to infection than other body components (Newberry & Lorenz (2005) *Immunol Rev* 206, 6-21). As an example, the digestive tract has roughly $10^{14}$ commensal organisms and frequently encounters pathogens. Furthermore, an additional challenge for the gut-associated lymphoid system is that typical food antigens should be tolerated while pathogenic antigens should induce vigorous immune responses. A hallmark of the mucosal immune system is the production of secretory immunoglobulin A (IgA). MALT plasma cells secrete primarily dimeric IgA in an $IgA_1:IgA_2$ ratio of 3:2, whereas IgA secreted in the tissue and blood compartment is primarily monomeric IgA in an $IgA_1:IgA_2$ ratio of 4:1. $IgA_2$ is more resistant to proteolysis by pathogens than $IgA_1$ (see, e.g., http://microvetarizona.edu/Courses/MIC419/Tutorials/bigpicture.html).

The mammalian immune system uses two general adaptive mechanisms to protect the body against environmental pathogens. When a pathogen-derived molecule is encountered, the immune response becomes activated to ensure protection against that pathogenic organism.

The first immune system mechanism is the non-specific (or innate) inflammatory response. The innate immune system appears to recognize specific molecules that are present on pathogens but not on the body itself.

The second immune system mechanism is the specific or acquired (or adaptive) immune response. Innate responses are fundamentally the same for each injury or infection; in contrast, acquired responses are custom-tailored to the pathogen in question. The acquired immune system evolves a specific immunoglobulin (antibody) response to many different molecules present in the pathogen, called antigens. In addition, a large repertoire of T cell receptors (TCR) is sampled for their ability to bind processed forms of the antigens bound to major histocompatibility complex (MHC, also known as human leukocyte antigen, HLA) class I and II proteins on the surface of antigen-presenting cells (APCs), such as dendritic cells (DCs).

The immune system recognizes and responds to structural differences between self and non-self proteins. Proteins that the immune system recognizes as non-self are referred to as antigens. Pathogens typically express large numbers of complex antigens.

Acquired immunity is mediated by specialized immune cells called B and T lymphocytes (or simply B and T cells). Acquired immunity has specific memory for antigenic structures; repeated exposure to the same antigen increases the response, which increases the level of induced protection against that particular pathogen.

B cells produce and mediate their functions through the actions of antibodies. B cell-dependent immune responses are referred to as "humoral immunity," because antibodies are found in body fluids.

T cell-dependent immune responses are referred to as "cell-mediated immunity," because effector activities are mediated directly by the local actions of effector T cells. The local actions of effector T cells are amplified through synergistic interactions between T cells and secondary effector cells, such as activated macrophages. The result is that the pathogen is killed and prevented from causing diseases.

The functional element of a mammalian lymph node is the follicle, which develops a germinal center (GC) when stimulated by an antigen. The GC is an active area within a lymph node, where important interactions occur in the development of an effective humoral immune response. Upon antigen stimulation, follicles are replicated and an active human lymph node may have dozens of active follicles, with functioning GCs. Interactions between B cells, T cells, and FDCs take place in GCs.

Various studies of GCs in vivo indicate that the many important events occur there, including immunoglobulin (Ig) class switching, rapid B cell proliferation (GC dark zone), production of B memory cells, accumulation of select populations of antigen-specific T cells and B cells, hypermutation, selection of somatically mutated B cells with high affinity receptors, apoptosis of low affinity B cells, affinity maturation, induction of secondary antibody responses, and regulation of serum immunoglobulin G (IgG) with high affinity antibodies. Similarly, data from in vitro GC models indicate that FDCs are involved in stimulating B cell proliferation with mitogens and it can also be demonstrated with antigen (Ag), promoting production of antibodies including recall antibody responses, producing chemokines that attract B cells and certain populations of T cells, and blocking apoptosis of B cells.

Similar to pathogens, vaccines function by initiating an innate immune response at the vaccination site and activating antigen-specific T and B cells that can give rise to long term memory cells in secondary lymphoid tissues. The precise interactions of the vaccine with cells at the vaccination site and with T and B cells of the lymphoid tissues are important to the ultimate success of the vaccine.

Almost all vaccines to infectious organisms were and continue to be developed through the classical approach of generating an attenuated or inactivated pathogen as the vaccine itself. This approach, however, fails to take advantage of the recent explosion in our mechanistic understanding of immunity. Rather, it remains an empirical approach that consists of making variants of the pathogen and testing them for efficacy in non-human animal models.

Given worldwide health problems caused by known and emerging infectious agents and even potential biological warfare pathogens, it is time for a fresh approach to understanding disease pathogenesis, the development and rapid testing of vaccines, and insights gathered from such work. Advances in the design, creation and testing of more sophisticated vaccines have been stalled for several reasons. First, only a small number of vaccines can be tested in humans, because, understandably, there is little societal tolerance for harmful side effects in healthy people, especially children, exposed to experimental vaccines. With the exception of cancer vaccine trials, this greatly limits the innovation that can be allowed in the real world of human clinical trials. Second, it remains challenging to predict which epitopes are optimal for induction of immunodominant CD4 and CD8 T cell responses and neutralizing B cell responses. Third, small animal testing, followed by primate trials, has been the mainstay of vaccine development; such approaches are limited by intrinsic differences between human and non-human species, and ethical and cost considerations that restrict the use of non-human primates. Consequently, there has been a slow translation of basic knowledge to the clinic, but equally important, a slow advance in the understanding of human immunity in vivo.

The artificial immune system (AIS) of the present invention can be used to address the inability to test many novel vaccines in human trials by instead using human tissues and cells in vitro. The AIS enables rapid vaccine assessment in an in vitro model of human immunity. The AIS provides an additional model for testing vaccines in addition to the currently used animal models.

Attempts have been made in modulating the immune system. See, for example, U.S. Pat. No. 6,835,550 B1, U.S. Pat. No. 5,008,116, WO 2004/101773 A1, Suematsu et al. (*Nat Biotechnol,* 22, 1539-1545, (2004)), and U.S. Patent Application No. 2003/0109042.

Nevertheless, none of these publications describe or suggest an artificial (ex-vivo) human cell-based, immune-responsive system comprising a vaccination site (VS) and a lymphoid tissue equivalent (LTE). The present invention comprises such a system and its use in assessing the interaction of substances with the immune system.

SUMMARY OF THE INVENTION

The present invention provides an artificial immune system for assessing potential vaccine agents without administration to animal subjects. The artificial immune system comprises a 3D matrix comprised of lymphoid tissue (a lymphoid tissue equivalent) and populations of B cells and/or T cells distributed within the 3D matrix. Also distributed within the 3D matrix are dendritic cells.

The present invention also provides a means by which the state of maturation of the dendritic cells within the artificial immune system can be controlled.

BRIEF DESCRIPTION OF THE DRAWINGS

FIG. 1. The state of the DCs can dictate naïve T cell migration behavior. DCs prepared using human serum (HS DCs) or fetal bovine serum (FBS DCs) were introduced into collagen gel containing autologous, negatively selected T cells. Initially, T cells were uniformly distributed throughout the gel. However, by day 12, the distribution patterns were distinct. HS DCs caused T cells to distribute preferentially towards the top of the collagen, while FBS DCs induced migration to a lesser degree.

FIG. 2. DCs prepared using human serum (HS DCs) or fetal bovine serum (FBS DCs) that had more of an immature or mature phenotype, respectively, were introduced into collagen gel containing autologous, negatively selected T cells. When tetanus toxoid-pulsed HS DCs or FBS DCs were introduced to the T cells, T cell proliferation was greater with FBS DCs than with HS DCs. Thus, the range of DC maturity states affects T cell activation and proliferation.

FIG. 3. OT-II reporter T cell responses were robustly detected at frequencies of about 1 antigen-specific cell per 100 T cells, and were still detectable at frequencies of about 1 antigen-specific cell per 10,000 T cells.

Figure 9B:
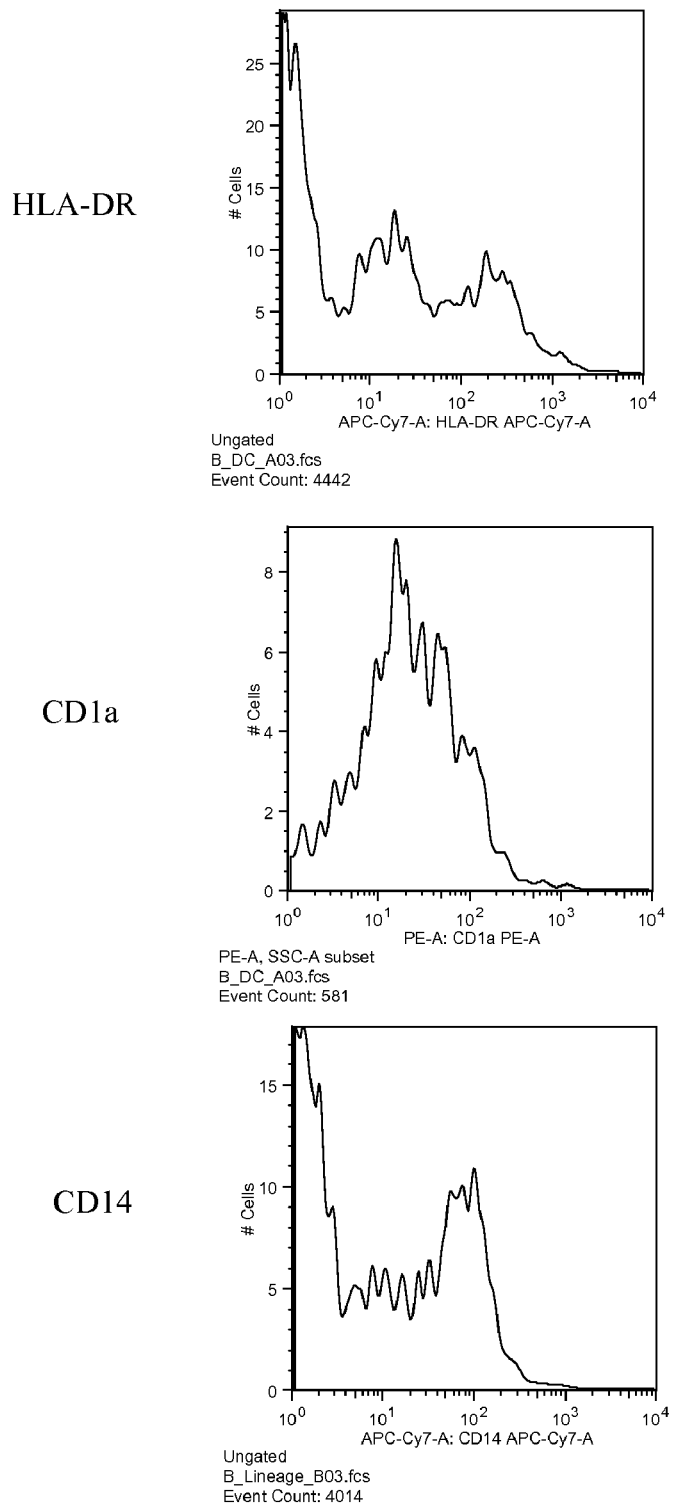
Figure 9C:
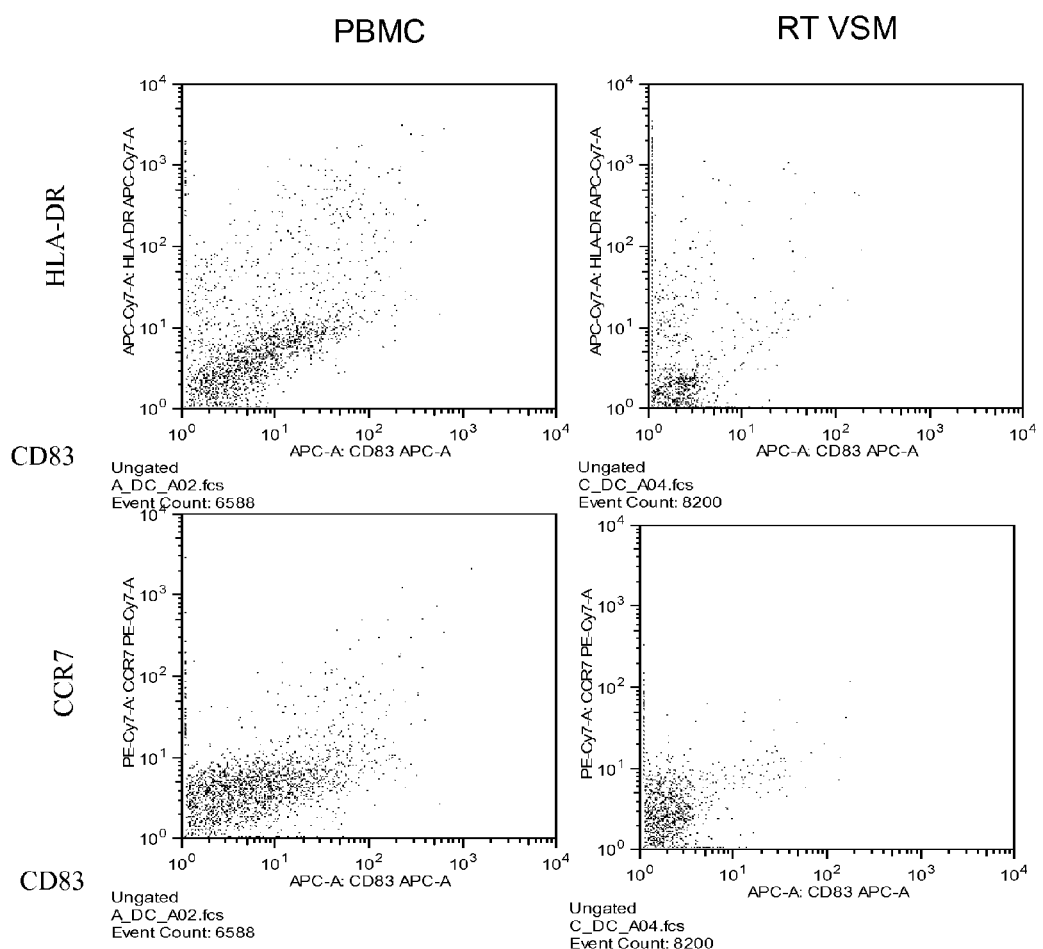
Figure 9D:
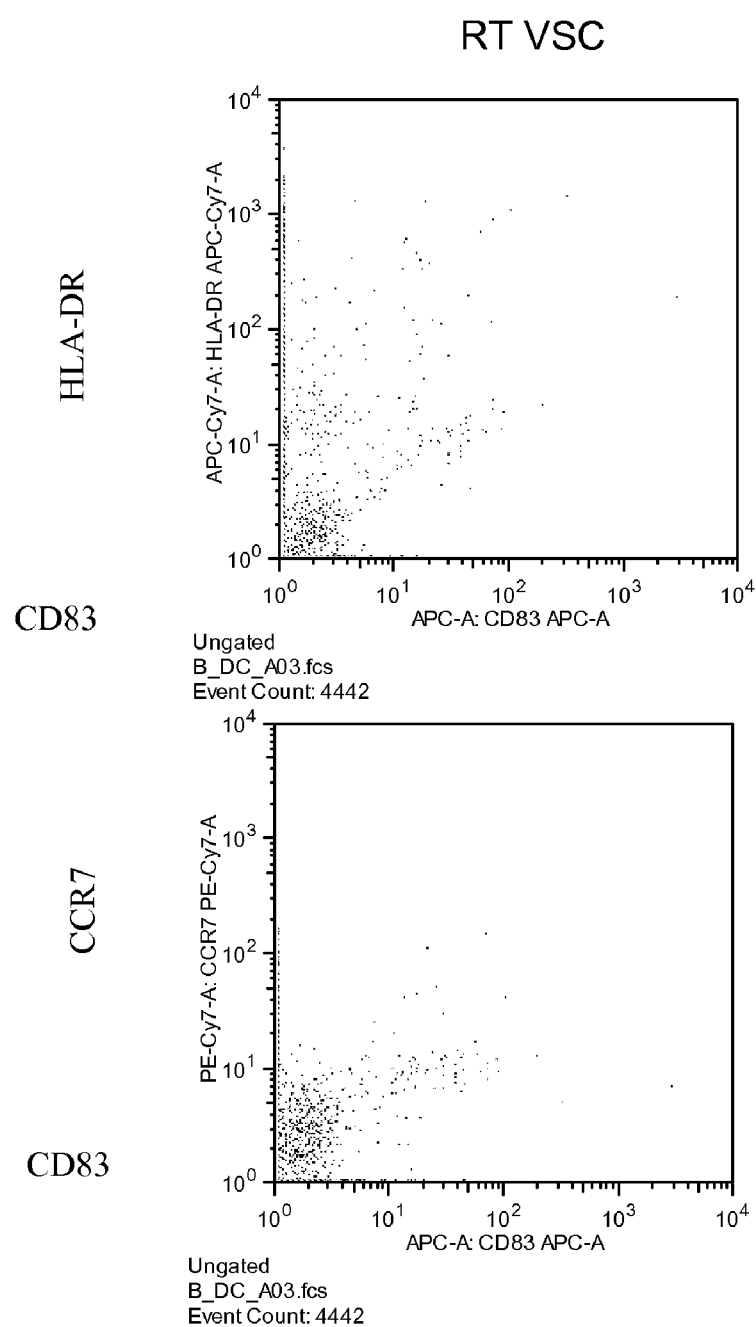

- Wild-type (C57Bl/6) or OT-II ovalbumin (ova)-specific $CD4^+$ T cells were mixed with mature ova-pulsed DCs (T:DC ratio ~10:1) in 96-well co-cultures. Proliferation and cytokine production were assayed after 3.5 days. The ratio of ova-specific OT-II T cells to wild-type cells was varied as shown.
- (A) CFSE dilution flow cytometry analysis. Undivided T cells have a fluorescence of ~103 units. Nearly all of the antigen-specific OT-II cells have divided multiple times in all cultures.
- (B) IL-2 production detected in co-cultures in 96-well round-bottom plates or round-bottom plates with collagen gels.

FIG. 4. Use of chemokine CCL21 to enhance the expansion of rare T cells in vitro. CCL21 chemokine enhances the expansion/survival of antigen-specific T cells in co-cultures, modeling rare, specific T cell-DC encounters.

FIG. 5. ECM production by BLS4 lymph node stromal cells. Antibody ER-TR7 was used to detect an ECM protein produced by lymph node stromal cells; it is known to colocalize with fibronectin in intact lymph nodes.

FIG. 6. Lymphocyte survival in vitro is enhanced by co-culture with BLS4 lymph node stromal cells. The graph shows number of live cells in control cultures (splenocytes alone) or splenocytes cultured on BLS4 monolayers over 11 days. Adding BLS4 cells resulted in ~4-fold more surviving splenocytes after 11 days.

FIG. 7. The ratio of immature to mature dendritic cells present in T-DC co-cultures impacts T cell proliferation and T cell survival.

FIG. 8. BLS4 stromal cells form reticular networks in protein-conjugated inverse opal scaffolds.

- (A) and (B) Stromal cells observed immediately after injection into scaffolds (a few cells are highlighted by false-color overlays). Note the initially rounded morphology.
- (C) and (D): After 24 hrs, BLS4 cells have attached to the scaffold and formed numerous intercellular connections stretching over and across pores of the scaffold. Shown are fluorescence micrographs taken through midplanes of two regions of scaffold layers (red=stromal cell f-actin, blue=cell nuclei, green=protein-conjugated scaffold surfaces).

FIGS. 9A-D. Immature population of reverse-transmigrated DCs from the vaccination site membrane (VSM) or the vaccination site cushion (VSC) is shown as $CD83^+$ with few $HLA-DR^+$ and $CCR7^+$ observed. CD14 is slightly decreased in VSM compared to VSC. These are for phenotypes before maturation signals are provided (e.g., TNFα).

FIGS. 10A-H. After maturation with *Candida albicans*/tetanus toxoid antigens/KLH and TNFα, there was an increase in the number of cells that are high in $CD14^+$ and HLA-DR. Additionally, some of these cells are expressing more $CD83^+/HLA-DR^+/CCR7^+$ after antigen priming.

DETAILED DESCRIPTION OF THE INVENTION

The present invention concerns the development of accurate, predictive in vitro models to accelerate vaccine testing, allow collection of more informative data that will aid in redesigning and optimizing vaccine formulations before animal or clinical trials, and raise the probability that a vaccine candidate will be successful in human trials. More specifically, the present invention comprises controlling the maturation state of the dendritic cells (DCs) in the lymphoid tissue equivalent (LTE, artificial lymph node) of the artificial immune system (AIS), because the state of DC maturation appears to impact their behavior there.

Tissue engineering involves the development of synthetic or natural materials or devices that are capable of specific interactions with cells and tissues. The constructs combine these materials with living cells to yield functional tissue equivalents. Tissue engineering involves a number of different disciplines, such as biomaterial engineering, drug delivery, recombinant DNA techniques, biodegradable polymers, bioreactors, stem cell isolation, cell encapsulation and immobilization, and the production of 2D and 3D scaffolds for cells. Porous biodegradable biomaterial scaffolds are required for the 3D growth of cells to form the tissue engineering constructs. There are several techniques to obtain porosity for the scaffolds, including fiber bonding, solvent casting/particulate leaching, gas foaming/particulate leaching, and liquid-liquid phase separation. These produce large, interconnected pores to facilitate cell seeding and migration. As used herein, the terms "tissue-engineered construct" or "engineered tissue construct" ("ETC") include any combination of naturally derived or synthetically grown tissue or cells, along with a natural or synthetic scaffold that provides structural integrity to the construct.

It is known that 3D biology is important to induce proper functionality of immunological ETCs (see, e.g., Edelman & Keefer, *Exp. Neurol.* 192, 1-6 (2005). A principal approach to studying cellular processes is to culture cells in vitro. Historically, this has involved plating cells on plastic or glass supports. Cells grown on solid or filter support are referred as two-dimensional (2D) cultures. Such 2D cultures on porous supports have been extremely useful for studying many aspects of biology. However, much more in vivo-like conditions can now be realized in 3D cultures. For example, many epithelial cells, both primary cultures and established lines, form complex epithelial structures when grown in 3D ECM.

Recently, in model in vitro lymph nodes, it has been shown that 3D interstitial tissue matrix facilitates not only T cell migration toward an APC, but also supports motility upon cell-cell interaction. A 3D collagen matrix environment, because of its spatial architecture, provides traction for lymphocyte crawling, mimicking some structural features of the lymph node cortex. This provides experimental justification for the importance of a 3D environment in the constructs that comprise the in vitro immune system.

The artificial immune system (AIS) of the present invention comprises a three-dimensional matrix comprised of lymphoid tissue. The matrix comprises a material selected from gelatin, collagen, synthetic ECM materials, PLGA, PGA, natural ECM materials, chitosan, protosan, and mixtures thereof. Distributed within the matrix comprising the lymphoid tissues are populations of at least one of B cells or T cells. Dendritic cells (mature and/or immature) are also distributed within the matrix.

Immature DCs (iDCs) and macrophages in the collagen cushion with naïve T cells tend to segregate the T cells into "zones" or clusters. An explanation may be that local chemokines and/or cytokines (such as CCL-21 and CXCL13) released from these APCs tend to act like "chemorepellants," helping to organize the T/B cell zones in a 3D matrix similar to what is seen in lymph nodes in vivo.

Mature DCs in the collagen cushion release cytokines and/or chemokines (such as CCL-21 and CXCL13) and activate naïve T cells to proliferate and secrete cytokines. Thus, the state of APC differentiation in the model lymph node appears to affect the lymph node architecture and activation of lymphocytes.

The present invention comprises methods to modulate the state of antigen-presenting cells (APCs), including dendritic cells (DCs). More specifically, the present invention includes methods of modulating the state of APCs (e.g., DCs) in the artificial immune system (AIS). The AIS of the present invention supports in situ priming of both naïve T and B cells and subsequent interactions between activated antigen-specific helper T cells and B cells to promote B cell expansion, antibody class switching, and somatic hypermutation. Thus, the maturation state of the dendritic cells in the AIS of the present invention can be controlled, for example, by the choice of culture medium, by the choice of serum added to the culture media (FIGS. 1, 2), by the addition of cytokines and/or chemokines added to the culture media (FIG. 4), or by the use of cells from a vaccination site.

The vaccination site (VS) is an in vitro skin and/or mucosal-equivalent scaffold that facilitates trafficking of blood monocytes and non-monocytic dendritic cell (DC) precursors and supports their natural conversion into mature antigen presenting dendritic cells within the artificial skin 3D tissue-engineered construct. Such a vaccination site will act as a skin-, gut-, or mucosal-equivalent tissue and comprises a skin construct (or a mucosal tissue, such as lung), together with vascular and lymphatic endothelium and blood-derived hematopoietic cells.

The skin construct can be derived from many sources, including complex sources, such as cadaveric human skin, less complex sources, such as commercially available skin-like products (EpiDerm, Episkin), or simple skin-like structures (using many different preparations of ECM and sources of skin fibroblasts and keratinocytes) optimized for integration into the in vitro system.

Blood cells (including monocytes) can be placed along the vascular endothelium. Such cells naturally migrate, convert to dendritic and other cells, and become resident in the skin.

If dendritic cells are present in the correct subtype and state of maturation for resting skin, the vaccination site is then ready to accept a vaccine candidate for testing. Upon vaccination, the vaccine will interact with skin-resident cells to induce further migration of monocytes and other cells into the skin, and their subsequent differentiation into more antigen-presenting cells (APCs), including macrophages and dendritic cells. Dendritic cells (DCs) and other antigen-presenting cells (APCs) pick up vaccine antigen and can be transferred to the lymphoid tissue equivalent (LTE). DCs in the LTE interact with T and B cells to initiate an adaptive immune response, and depending on the maturation state of the DCs, they will activate T and B cells to differing extents.

A step-wise approach to a VS is to build a 3D structure that comprises vascular and lymphatic endothelial cells that can support transendothelial trafficking of monocytes and other DC precursors in a manner that recapitulates in vivo differentiation, maturation and migratory functions.

It is known that a 3D tissue construct that permits heterologous cell-cell interactions impacts the differentiation of DC precursors, including monocytes, in a manner that more closely mimics an intact human system than is observed in 2D culture (see, e.g., Edelman & Keefer, *Exp. Neurol.* 192:1-6 (2005)). Specifically, co-culture of whole PBMCs with vascular endothelial monolayers, grown on either reconstituted type I collagen matrices (Randolph, et al., *Blood* 92: 4167-4177 (1998a); Randolph, et al., *Science* 282:480-483 (1998b); Randolph, et al., *Proc. Natl. Acad. Sci. USA* 95:6924-6929 (1998c); Randolph, et al., *J. Exp. Med.* 196: 517-527 (2002)) or native amniotic connective tissue (Randolph & Furie, *J. Exp. Med.* 183:451-462 (1996)) promotes the passage particularly of monocytes across the endothelium, largely in response to endogenous production of the chemoattractant monocyte chemoattractant protein (MCP)-1 (CCL2) (Randolph & Furie, *J. Immunol.* 155:3610-3618 (1995)). This is consistent with the knowledge that many monocytes leave the blood each day, under normal steady state conditions. When the endothelium is activated, other inflammatory cell types, such as neutrophils, can traverse the endothelium, again with the same regulatory events that are understood to operate in vivo (Furie & McHugh, *J. Immunol.* 143:3309-3317 (1989)). If the fate of monocytes is followed with time in endothelial cell/collagen cultures, it becomes apparent that a substantial fraction of monocytes increase production of a range of molecules (including MHC II, CD40, CD83, CD86) known to be upregulated in DCs and these cells also acquire migratory properties such that they migrate out of the cultures, crossing the endothelium in the ablumenal to lumenal direction, away from the vascular endothelium and away from the macrophages that remain resident in the subendothelial matrix.

Figure 10B:
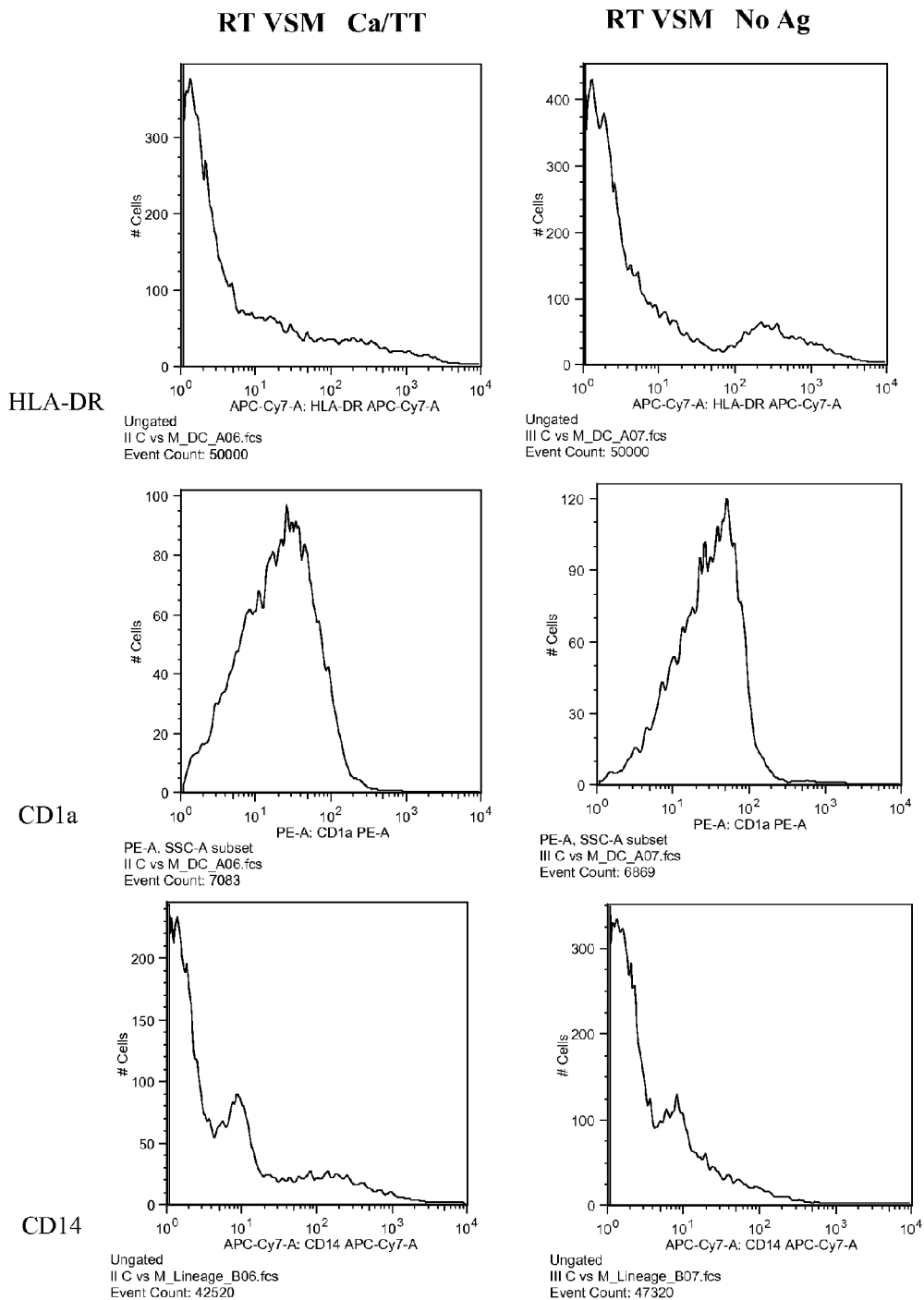
Figure 10C:
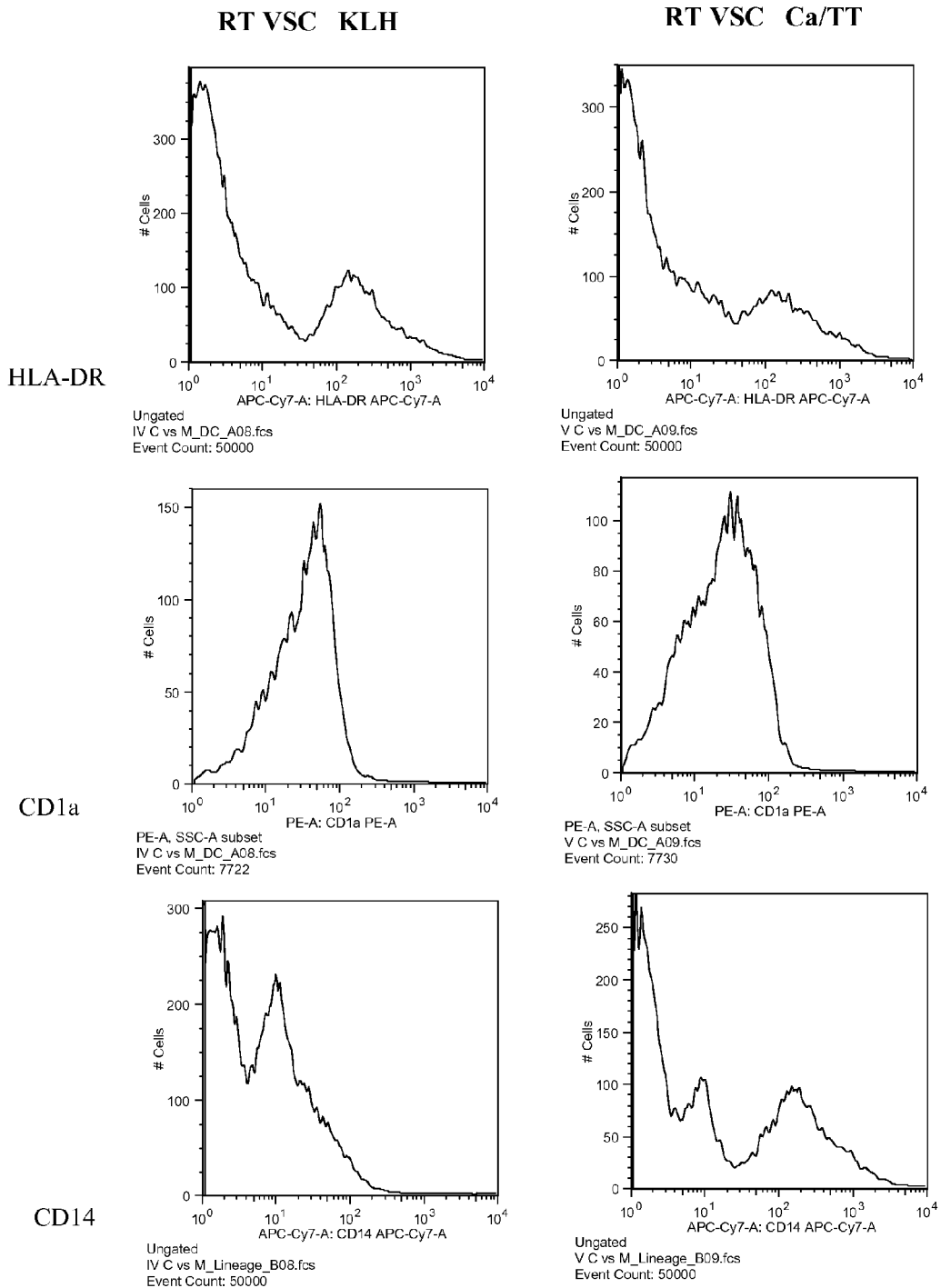
Figure 10D:
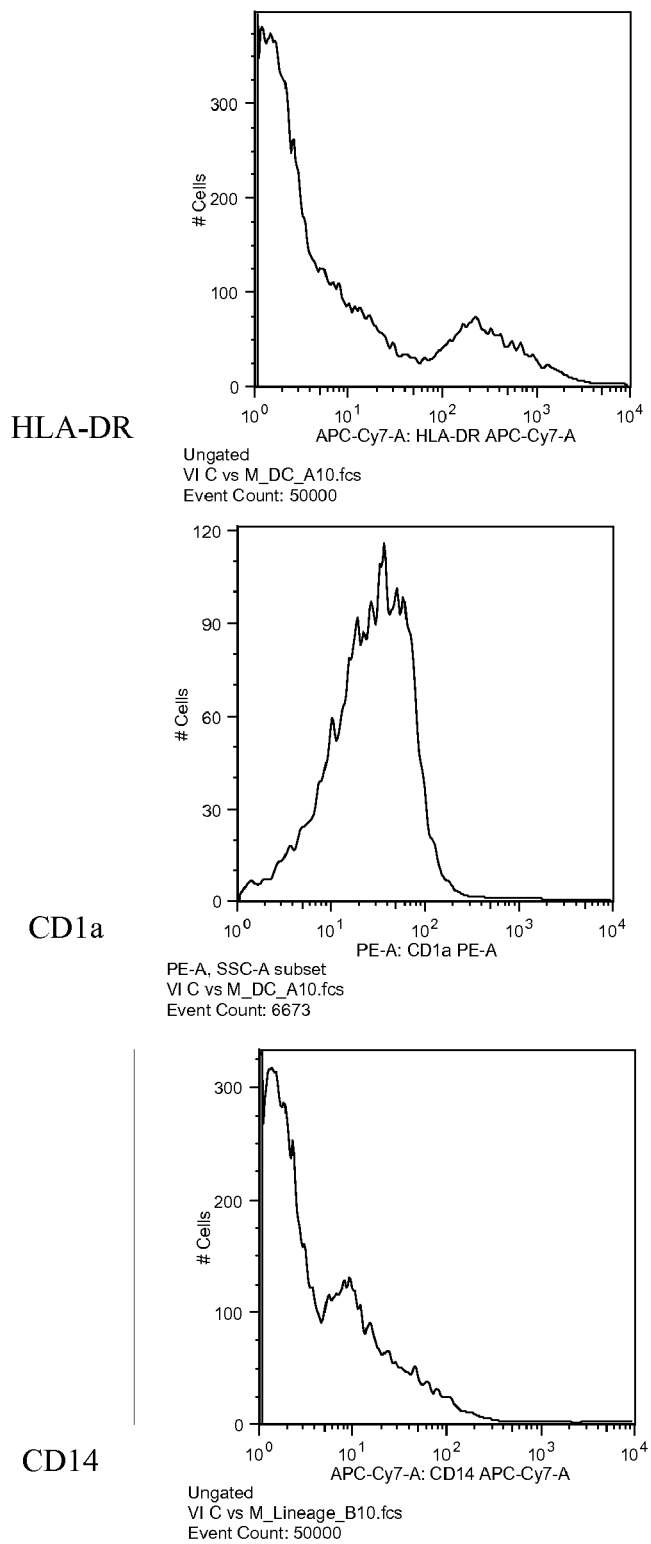
Figure 10E:
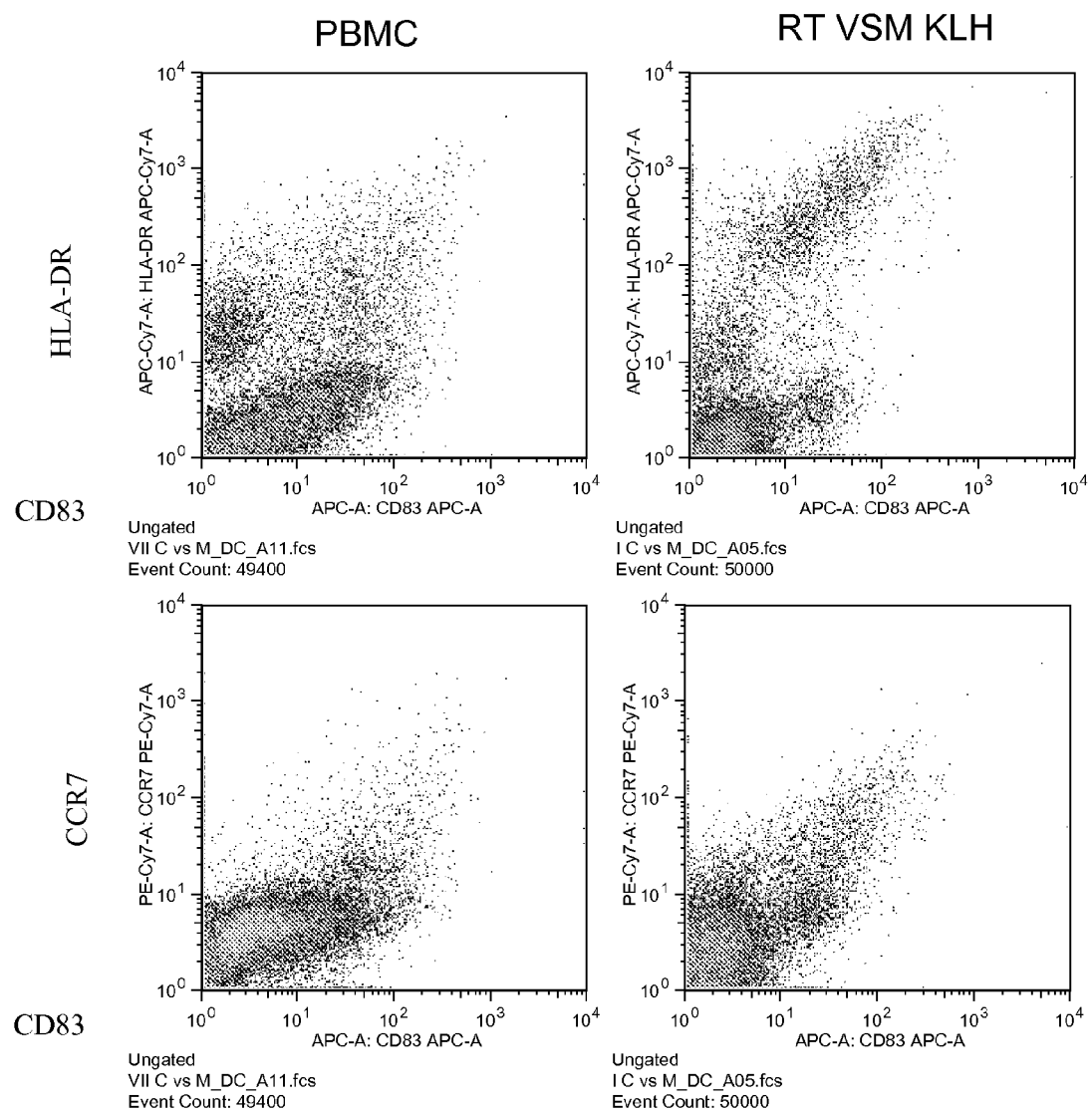
Figure 10F:
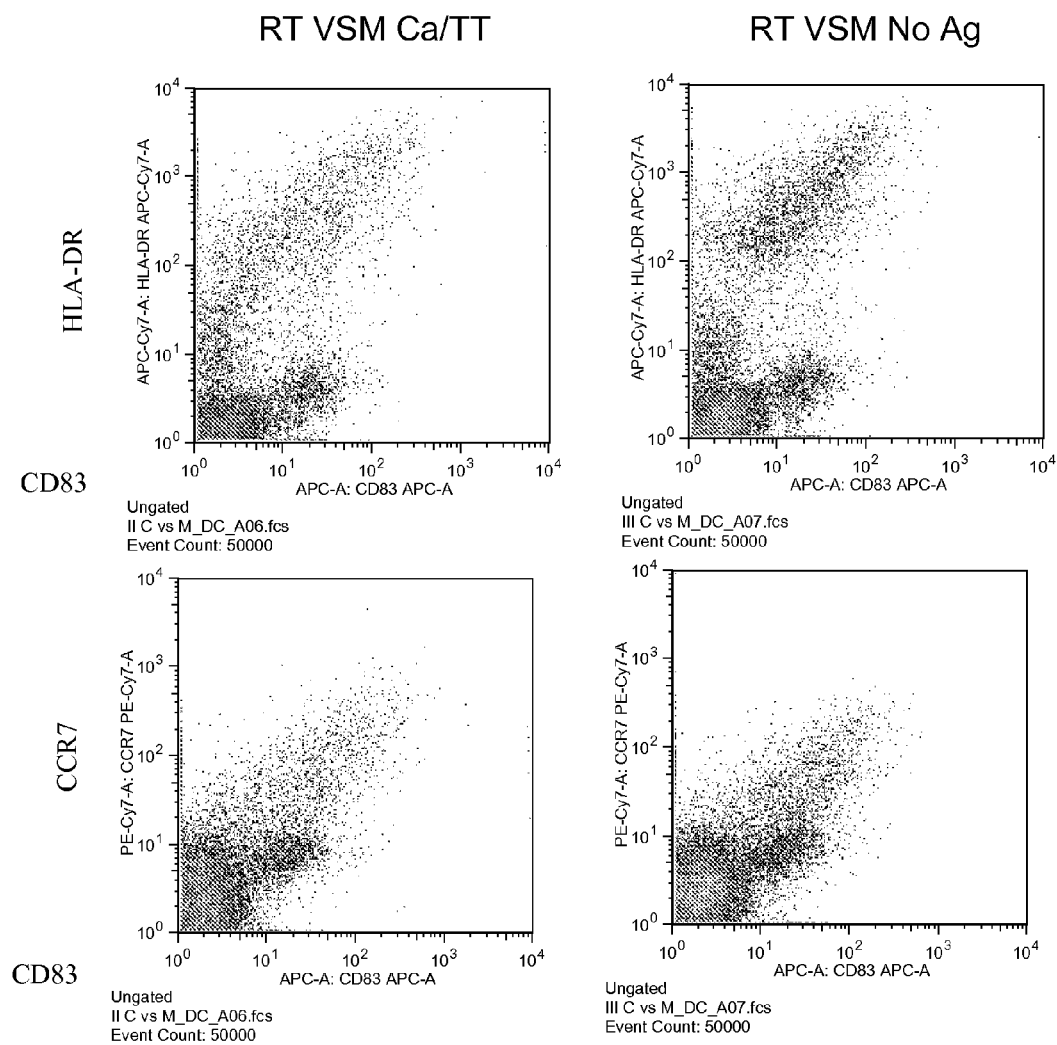
Figure 10G:
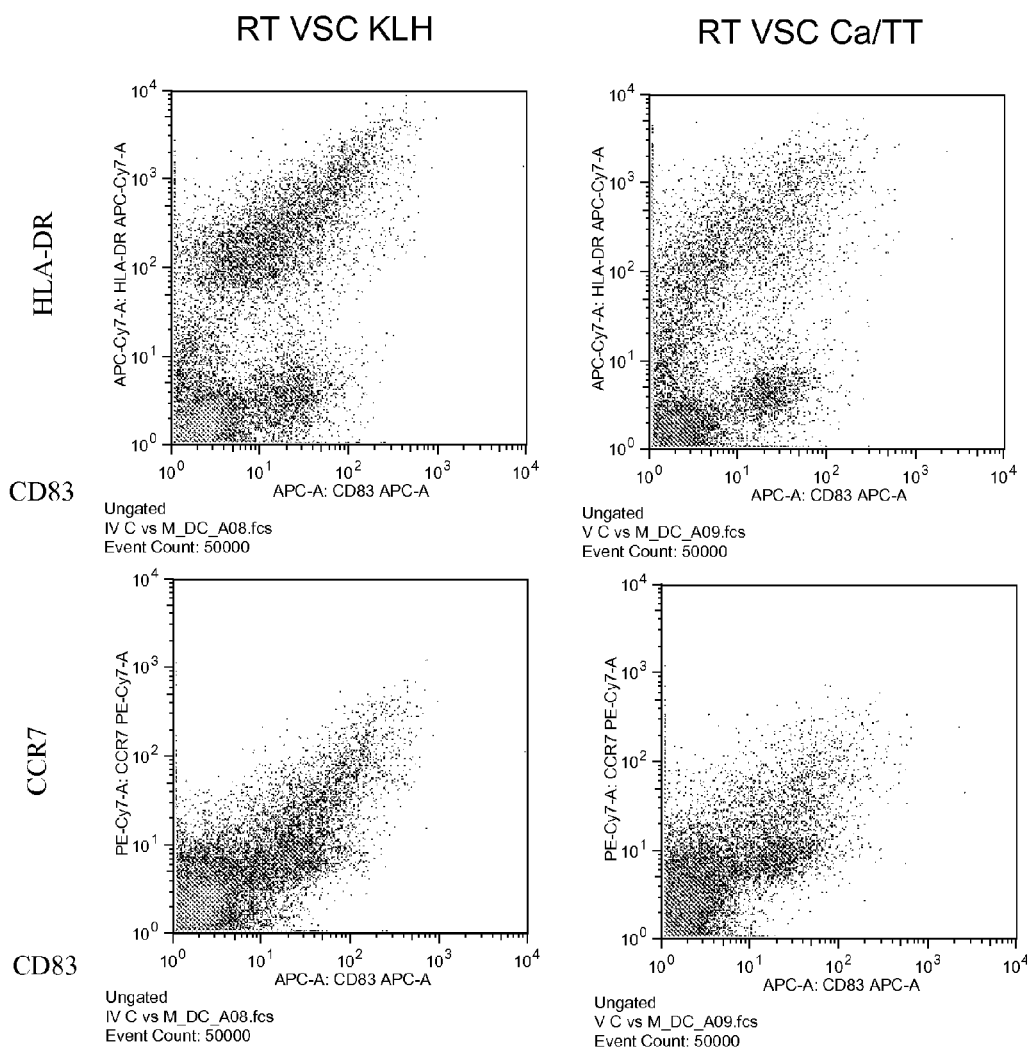
Figure 10H:
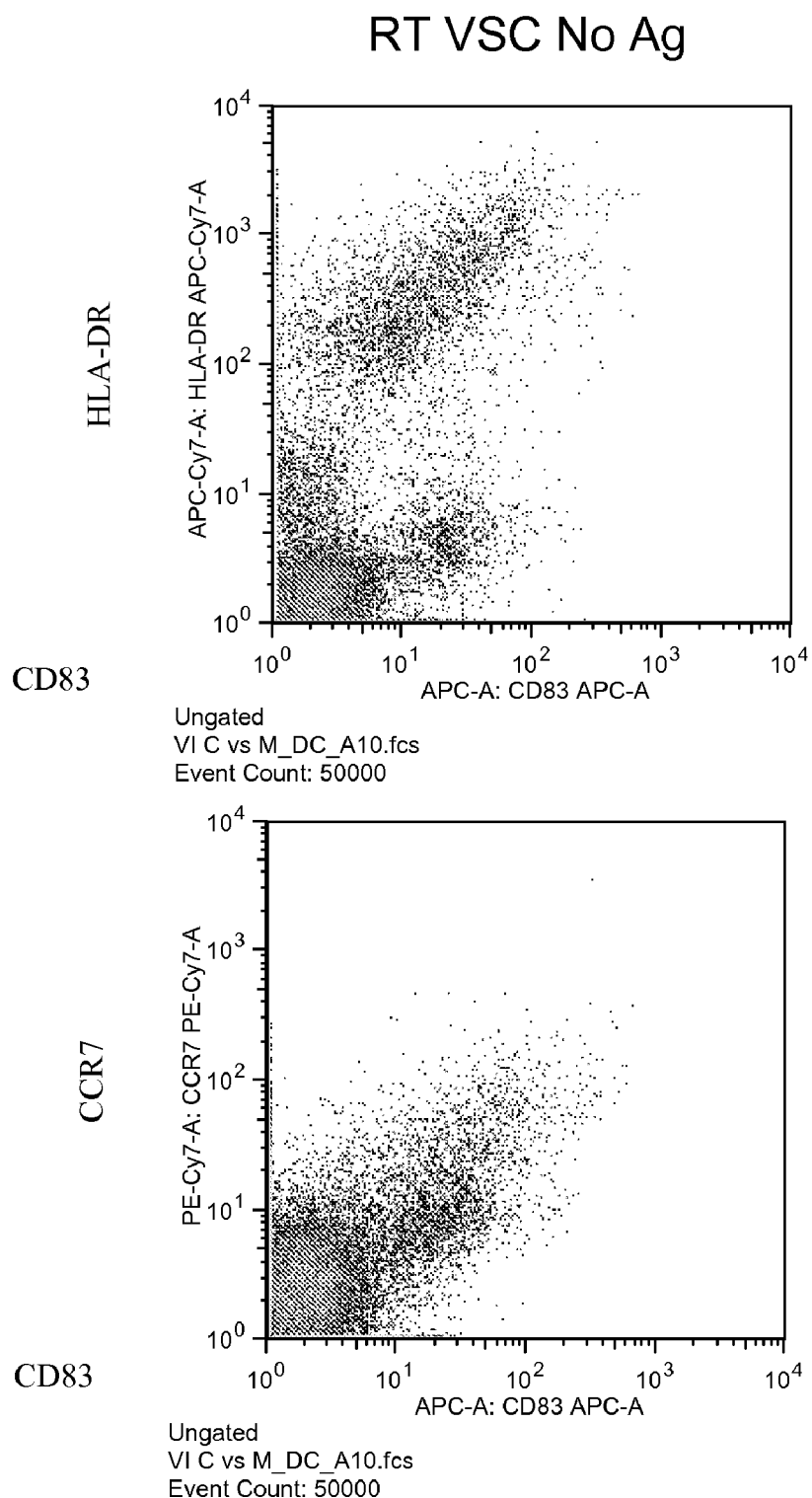

As shown in FIG. 10A of U.S. Appln. Publication No. 2005/0282148, vascular endothelial cells grown on 3D constructs of fibronectin-coated collagen form intercellular junctions that remain intact after passage of monocytes into subendothelial matrix to increasing depths (arrowheads, monocytes visualized by differential interference contrast microscopy). En face views and a cross-section of the cultures are shown, where emigrated leukocytes are distributed throughout the matrix under the characteristically flat endothelial monolayer. As described in design features 1 and 2, a lymphatic endothelial monolayer or an epidermal monolayer, respectively, on the currently bare lower surface of such a matrix. FIG. 10B is a schematic diagram showing the stages of monocyte behavior in such a 3D culture. The image on the left depicts the sequence of observations when the matrix does not contain a source of microbial antigen, whereas the images on the right depict the sequence of observations made when yeast particles (zymosan) are incorporated as a model microbial antigen in the matrix. In stage I, incubation of peripheral blood mononuclear cells (PBMCs) are incubated with endothelium for 1.5 hours results in the transmigration of most monocytes (3), some BDCA1+ blood dendritic cells (data not shown), natural killer cells (Berman et al., *J. Immunol.* 156:1515-1524, (1996)), but few lymphocytes, into the subendothelial collagen. Of the few lymphocytes that do migrate, these are likely of a memory phenotype (Gergel & Furie, *Infect. Immun.* 69:2190-2197, (2001)), consistent with our understanding that naive T cells traffic into lymph nodes directly and memory T cells can enter tissues. In stage II, the cell culture is washed, and monocytes accumulated in the subendothelial matrix are left with an intact endothelial monolayer, where the monocytes engulf phagocytic particles if such particles have been included in the collagen matrix. In stage III, some of the phagocytic monocyte-derived cells retraverse the same endothelium and accumulate in the apical compartment. These reverse-transmigrated monocytes previously or simultaneously differentiate into DC. Photographs (upper right, B) show their characteristic morphology. When no activation stimuli are included in the cultures (left), the reverse-transmigrated cells are immature DCs and promote T cells to produce IL-10 as observed by intracellular cytokine staining. Many of these cells are non-adherent, like DCs, but a few spreading cells are similar to less differentiated monocytes (left photo inset, B). When activation stimuli are included in the cultures, the reverse-transmigrated cells become mature DCs and promote development mainly of IFNy producing T cells.

As it is now possible to differentially isolate vascular and lymphatic endothelium (Podgrabinska, et al., *Proc. Natl. Acad. Sci. USA*, 99:16069-16074 (2002)), and given the knowledge and resources for preparing these cells, a functional VS comprising vascular and lymphatic endothelial cells can be constructed. The vascular and lymphatic endothelial cells support transendothelial trafficking of monocytes and other DC precursors in a manner that recapitulates in vivo differentiation and migratory functions. Several matrices can be used, including xenographic ECM sheets, natively polymerized human amniotic connective tissue (Randolph & Furie, *J. Exp. Med.* 183:451-462 (1996)), reconstituted collagen matrices, protasan/collagen membrane scaffolds, or preferably matrices that contain fibroblasts and/or mast cells. Several commercial preparations of dermal tissues containing fibroblasts are available and these are readily prepared in vitro, for example by seeding fibroblasts with matrix components and allowing the fibroblasts to modify and contract these components, as described earlier.

It is anticipated that the process of incorporating cells within the matrix could be adapted for the incorporation of a variety of cells such as fibroblasts or mast cells. In a preferred embodiment, vascular and endothelial monolayers are constructed that mimic the normal physiology of these vessels in coordinating recruitment and trafficking of immune cells during immunization. In another embodiment, the endothelium can be derived from human foreskin (Podgrabinska, et al., *Proc. Natl. Acad. Sci. USA*, 99:16069-16074 (2002)) or from adult skin.

The present invention comprises co-culture conditions to mimic the expansion of antigen-specific lymphocyte populations observed in vivo. It is a challenge to mimic the robust expansion of antigen specific T cells from their rare initial population to the significant numbers present during the peak of in vivo immune responses. Such expansion can be dramatic in vivo; for example, in experimental lymphocytic choriomeningitis virus infection in mice, 100-200 naïve T cells specific for one antigen transiently expand to ~$10^7$ effector T cells, an expansion of about 50,000-fold (Blattman et al. (2002) *J Exp Med* 195, 657-664).

Furthermore, this is more rigorous than simply expanding T cells to a detectable population that could be correlated with a particular antigenic stimulation.

It requires that the cells, in fact, expand to a population size comparable to that observed in vivo to provide physiologic help for CTL and B cell priming.

The present invention comprises strategies comprising varying the cellular composition and presence of cytokines and/or chemokines in in vitro T cell cultures to better mimic the in vivo environment. These strategies enhance the expansion and survival of T cells primed under conditions of rare antigen-specific T cell-dendritic cell encounters.

In embodiments of the present invention, the cells are grown in dense co-cultures prepared in 96-well culture plates, to facilitate automation and rapid assessment of outcomes. Embodiments of the present invention include strategies to magnify the numbers of T cells expanded in single-step in vitro cultures. The strategies described can be implemented in a range of LTE formats, including inverse opal scaffolds, collagen matrices, and traditional well-format plate cultures.

The practice of the present invention will employ, unless otherwise indicated, conventional methods of immunology, histology, microbiology, cell and tissue culture, and molecular biology within the ordinary skill of the art. Such techniques are explained fully in the literature. All publications, patents, and patent applications cited herein are incorporated by reference in their entirety.

EXAMPLES

Example 1

Detection limits with antigen-specific reporter cells. We developed a system to track rare antigen-specific T cells mixed with dilute antigen-presenting dendritic cells (DCs), as a means to define culture conditions for T cell priming in vitro. We used a murine transgenic $CD4^+$ T cell (OT-II, which recognizes peptides from ovalbumin (ova)) for this purpose, to identify general culture conditions that can be applied to both the mouse and human systems. In this example, to mimic the rare occurrence of antigen-specific T cells, these 'reporter' cells were mixed with varying ratios of wild-type C57BL/6 $CD4^+$ T cells, and bone marrow-derived dendritic cells. Cultures were prepared with a fixed ratio of T cells to DCs of ~10:1, approximately matching the ratio of these cells in lymph nodes in vivo. An advantage of this system is that it allows quantitative labeling, isolating, and identifying antigen-specific cells in these cultures at all times, which is simply not possible in vivo.

We tested whether we could detect antigen-specific T cell priming at T cell dilutions approaching the in vivo frequency of mouse and human naïve T cells.

OT-II ova-specific T cells were labeled with the fluorescent dye CFSE (used to track cell proliferation; each time a cell divides, its fluorescence is halved). OT-II T cells, wild-type T cells, and ova-pulsed mature DCs were mixed and cultured for 3.5 days.

As shown in FIG. 3A, when OT-II T cells make up 10% of the T cells in the co-culture (red curve), numerous rounds of cell division were detected, as indicated by the multi-peaked histogram. Undivided cells in this experiment had a fluorescence of ~$10^3$ units; thus nearly all the antigen-specific cells have divided several times.

As shown in the other curves, significant numbers of OT-II T cells that had proliferated were still detected when they made up only about 1% of the T cell population, and further, detectable OT-II cells were found even when their frequency was only ~1 in 10,000 among the T cells initially added to the culture. Measurement of IL-2 production (FIG. 3B) and interferon-γ (IFN-γ) production (data not shown) showed a dose-dependent response that decayed as the number of OT-II cells present declined.

Thus, this system allows the mimicking of rare antigen-specific T cell encounters, even with precursor T cell frequencies similar to the rarity of natural naïve T cells in vivo.

Example 2

When we compared T cell priming in dense 96-well cultures ($2 \times 10^5$ to ~$5 \times 10^5$ cells per well) to priming in collagen gels also prepared in 96-well plates, IL-2 production was about 50% of the level seen in the no-matrix case. This result is consistent with published data on T cell priming in collagen (Gunzer et al. (2000) *Immunity* 13, 323-332) and may reflect slower migration of T cells through the matrix in their search for antigen-bearing DCs, relative to the cells-only aggregates formed in no-matrix cultures.

Example 3

In another embodiment of the present invention, the strategy to enhance expansion of rare T cells in vitro comprises T cell-dendritic cell co-cultures, comprising a mixture of immature and mature DCs, to enhance the proliferation and survival of antigen-specific T cells. Immature DCs also aid in zone formation typical of in vivo lymph nodes (see FIG. 1). The collagen matrix model has enabled us to show basic results that suggest the maturation state of the DC may impact its behavior in the lymph node. Immature DCs/macrophages in the collagen cushion with naïve T cells tend to segregate the T cells into "zones" or clusters. One possible explanation is the local chemokines released from these APCs tend to act like "chemorepellants" helping to organize the T/B cell zones in a 3D matrix similar to that found in the lymph node. Mature DCs in the collagen cushion with naïve T cells activate these T cells to proliferate and secrete cytokines. Thus, the state of APC differentiation in the lymph node appears to assist in the formation of the lymph node architecture, or activation of lymphocytes.

Example 4

Phenotypic and Functional Characterization of RT-DCs

To examine the determination of functional capacity and phenotypic characteristics of the vaccination site, experiments were conducted to examine markers of DC differentiation and maturation. The phenotypic markers used to characterize cells related to the VS were the macrophage profile (CD68, CD206, CD36, CD205, CD209), DC profile (CD83, CD1a, CD205, CD207, CD208, CD209), maturation status profile (HLA-DR, CD40, CD80, CD86 CD16, CD32, CD64), chemokine receptor profile (CCR7, CCR2, CXCR4, CXCR5, CCR6), lineage profile (CD56, CD3, CD19, CD14, CD31, CD144) and survival markers such as annexin V or 7AAD. Reverse transmigrated DCs (RT-DCs) were generated from the vaccination site collagen membrane and collagen cushion modules, presented with antigens (Candida albicans, tetanus toxoid combination, KLH), and driven to maturity with TNFα (FIGS. 9, 10)

Example 5

Creation of lymph node-like stromal cell networks in the LTE and their impact on lymphocyte function. ECM production by BLS4 cells: Creation of 3D reticular structures by lymph node stromal cells cultured in 3D inverse opal LTE scaffolds In addition to secreting factors that support lymphocyte survival and/or priming, lymph node stromal cells likely assist in providing the physical network in 3D cultures to support T cell and DC motility and subsequent interactions (FIG. 6).

When BLS4 (murine) stromal cells are placed in standard 2D culture plates, they spread to form confluent layers typical of fibroblasts (FIG. 8) However, when BLS4 cells were injected into fibronectin/laminin-conjugated inverse opal LTE hydrogel scaffolds, their behavior and morphology were entirely different. Immediately after injection, the cells were rounded and situated within the void spaces of the scaffold (FIG. 8). Within 1 hr, we observed the cells attaching, spreading, and forming numerous intercellular connections spanning multiple pores of the scaffold in all three dimensions. After 24 hrs, cells in scaffolds were fixed and stained with fluorescent markers for f-actin and cell nuclei to visualize the cells in 3D.

As can be seen in FIGS. 5 and 8, extensive cell-cell 3D interconnections similar to the 3D web-like nature of the natural stromal network in lymph nodes were evident.

In an experiment where stromal cells, lymphocytes, and dendritic cells were 're-aggregated' in culture without scaffolds to guide the stromal cell assembly, we observed lymphocytes with highly extended lamellipodia in fixed samples, suggesting that co-culture with stromal cells strongly influences lymphocyte attachment and polarization.

Example 6

OT-II and wild-type T cells (at a ~1:10 ratio) were mixed with DCs (total T:DC ratio ~10:1) in 96-well plate co-cultures and the ratio of immature to mature ova protein-pulsed DCs was varied. OT-II T cell proliferation was tracked by CFSE dilution. Surprisingly, significantly greater T cell proliferation/survival was found when the ratio of immature to mature DCs was ~1:1, with fewer DCs initially bearing antigen than in the ~1:10 iDC:mDC case (FIG. 7).

The above description and examples are for the purpose of teaching the person of ordinary skill in the art how to practice the present invention, and it is not intended to detail all those obvious modifications and variations of it that will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A three-dimensional lymphoid tissue equivalent (LTE), comprising: a three-dimensional matrix and lymphoid cells from a single donor distributed therein, wherein said lymphoid cells consist of:
   (i) a population of B cells and T cells, and
   (ii) a population of dendritic cells, wherein said population of dendritic cells comprises both mature and immature dendritic cells.

2. The LTE of claim 1, wherein said matrix is in the form of an inverse opal scaffold or a collagen matrix.

3. The LTE of claim 1, wherein said matrix comprises a material selected from gelatin, collagen, synthetic ECM materials, PLGA, PGA, natural ECM materials, chitosan, protosan, and mixtures thereof.

4. The LTE of claim 1, wherein the ratio of mature to immature dendritic cells is adjusted, prior to distribution of the dendritic cells in the three-dimensional matrix, so as to control the segregation and activation of the population of T cells and B cells.

5. The LTE of claim 4, wherein the segregation of T cells is controlled by release of cytokines and/or chemokines by the immature dendritic cells.

6. The LTE of claim 4, wherein the activation of T cells is controlled by the release of cytokines and/or chemokines by the mature dendritic cells.

7. The LTE of claim 5, wherein the cytokines and/or chemokines is CXCL13.

8. The LTE of claim 6, wherein the cytokines and/or chemokines is CXCL13.

9. The LTE of claim 1, wherein said LTE further comprises stromal cells distributed in said matrix.

10. The LTE of claim 9, wherein said stromal cells are BLS4 stromal cells.

11. The LTE of claim 9, wherein said stromal cells are human stromal cells from the same donor as the lymphoid cells.

12. The LTE of claim 9, wherein said stromal cells form a physical scaffold to support T cell and dendritic cell motility and interactions.

13. A method of evaluating the potential reaction of an animal to an agent, said method comprising:
   administering an agent to the LTE of claim 1; and
   evaluating the B cell and/or T cell responses to said agent.

14. The method of claim 13, wherein said method further comprising administering one or more cytokines and/or chemokines to the LTE.

15. The method of claim 14, wherein said one or more cytokines and/or chemokines comprises CCL21.

16. The method of claim 14, wherein said chemokine is selected from the group consisting of CCL21 and CXCL13.

17. The method of claim 13, wherein said agent is selected from the group consisting of a vaccine, an adjuvant, an immunotherapy candidate, a cosmetic, a drug, a biologic, and a chemical compound.

18. The LTE of claim 1, wherein the dendritic cells are from a vaccination site culture.

* * * * *